United States Patent
Brucker et al.

(10) Patent No.: US 7,338,485 B2
(45) Date of Patent: *Mar. 4, 2008

(54) CARDIAC LESIONS WITH CONTINUITY TESTING

(75) Inventors: Gregory G. Brucker, Minneapolis, MN (US); Robert H. Svenson, Holland Patent, NY (US)

(73) Assignee: Medical CV, Inc., Inver Grove Heights, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 11/066,959

(22) Filed: Feb. 25, 2005

(65) Prior Publication Data

US 2005/0171521 A1    Aug. 4, 2005

Related U.S. Application Data

(63) Continuation of application No. 10/975,674, filed on Oct. 28, 2004, now Pat. No. 7,267,674.

(60) Provisional application No. 60/516,242, filed on Oct. 31, 2003.

(51) Int. Cl.
*A61B 18/22* (2006.01)
(52) U.S. Cl. .......................... 606/12; 128/898; 606/10; 606/13
(58) Field of Classification Search ............ 606/13–15; 128/898
See application file for complete search history.

(56) References Cited

U.S. PATENT DOCUMENTS 4,693,244 A    9/1987    Daikuzono (Continued)

FOREIGN PATENT DOCUMENTS

EP    1 170 034 A2    1/2002

(Continued)

OTHER PUBLICATIONS

Abela, *Lasers in Cardiovascular Medicine and Surgery: Fundamentals and Techniques*, p. 28 (1990).

(Continued)

*Primary Examiner*—Henry M. Johnson, III
(74) *Attorney, Agent, or Firm*—Merchant & Gould P.C.

(57) ABSTRACT

A method and apparatus for treating in situ biologic tissue include identifying a patient with a condition susceptible to treatment by forming a lesion in the tissue and accessing a surface of the tissue. A lesion formation tool is positioned against the accessed surface. The tool includes an optical fiber for guiding a coherent waveform of a selected wavelength to a fiber tip for discharge of light energy from the fiber tip. The wavelength is selected for the light energy to penetrate a full thickness of the tissue to form a volume of necrosed tissue through the thickness of the tissue. The tool further includes a guide tip coupled to the fiber tip. The guide tip is adapted to have a discharge bore aligned with the fiber tip to define an unobstructed light pathway from the fiber tip to the tissue surface. The guide tip is further adapted to be placed against the tissue surface with the guide tip slidable along the tissue surface in atraumatic sliding engagement with the discharge bore opposing the tissue surface. The lesion formation tool is manipulated to draw the guide tip over the tissue surface in a pathway while maintaining the discharge bore opposing the tissue surface to form a transmural lesion in the tissue extending a length of the pathway.

9 Claims, 16 Drawing Sheets

U.S. PATENT DOCUMENTS

| | | | |
|---|---|---|---|
| 4,785,815 A | 11/1988 | Cohen | |
| 4,955,267 A | 9/1990 | Jacobs et al. | |
| 4,985,028 A | 1/1991 | Isner et al. | |
| 4,997,431 A | 3/1991 | Isner et al. | |
| 5,046,810 A | 9/1991 | Steiner et al. | |
| 5,104,393 A | 4/1992 | Isner et al. | |
| 5,125,926 A | 6/1992 | Rudko et al. | |
| 5,172,699 A | 12/1992 | Svenson et al. | |
| 5,281,212 A | 1/1994 | Savage et al. | |
| 5,282,798 A | 2/1994 | Bruse et al. | |
| 5,290,277 A | 3/1994 | Vercimak et al. | |
| 5,306,274 A | 4/1994 | Long | |
| 5,318,525 A | 6/1994 | West et al. | |
| 5,354,296 A | 10/1994 | Turkel | |
| 5,360,426 A | 11/1994 | Müller et al. | |
| 5,368,564 A | 11/1994 | Savage | |
| 5,380,316 A | 1/1995 | Aita et al. | |
| 5,389,096 A | 2/1995 | Aita et al. | |
| 5,409,008 A | 4/1995 | Svenson et al. | |
| 5,423,805 A | 6/1995 | Brucker et al. | |
| 5,500,012 A | 3/1996 | Brucker et al. | |
| 5,501,271 A | 3/1996 | Wijkstrom | |
| 5,507,725 A | 4/1996 | Savage et al. | |
| 5,534,000 A | 7/1996 | Bruce | |
| 5,537,499 A | 7/1996 | Brekke | |
| 5,651,786 A | 7/1997 | Abela et al. | |
| 5,728,091 A | 3/1998 | Payne et al. | |
| 5,769,843 A | 6/1998 | Abela et al. | |
| 5,782,828 A | 7/1998 | Chen et al. | |
| 5,800,428 A | 9/1998 | Nelson et al. | |
| 5,824,005 A | 10/1998 | Motamedi et al. | |
| 5,827,267 A | 10/1998 | Savage et al. | |
| 5,830,209 A | 11/1998 | Savage et al. | |
| 5,897,551 A | 4/1999 | Everett et al. | |
| 5,925,033 A | 7/1999 | Aita et al. | |
| 5,931,848 A | 8/1999 | Saadat | |
| 5,951,541 A | 9/1999 | Simpson et al. | |
| 6,024,739 A | 2/2000 | Ponzi et al. | |
| 6,063,080 A | 5/2000 | Nelson et al. | |
| 6,063,081 A | 5/2000 | Mulier et al. | |
| 6,066,131 A | 5/2000 | Mueller et al. | |
| 6,068,629 A | 5/2000 | Haissaguerre et al. | |
| 6,110,167 A | 8/2000 | Cozean et al. | |
| 6,135,996 A | 10/2000 | Kolesa et al. | |
| 6,161,543 A | 12/2000 | Cox et al. | |
| 6,200,308 B1 | 3/2001 | Pope et al. | |
| 6,200,310 B1 | 3/2001 | Ben-haim et al. | |
| 6,231,518 B1 | 5/2001 | Grabek et al. | |
| 6,231,568 B1 | 5/2001 | Loeb et al. | |
| 6,237,605 B1 | 5/2001 | Vaska et al. | |
| 6,258,083 B1 | 7/2001 | Daniel et al. | |
| 6,311,692 B1 * | 11/2001 | Vaska et al. | 128/898 |
| 6,314,962 B1 | 11/2001 | Vaska et al. | |
| 6,314,963 B1 | 11/2001 | Vaska et al. | |
| 6,474,340 B1 * | 11/2002 | Vaska et al. | 128/898 |
| 6,514,244 B2 | 2/2003 | Pope et al. | |
| 6,514,250 B1 | 2/2003 | Jahns et al. | |
| 6,517,536 B2 | 2/2003 | Hooven et al. | |
| 6,546,935 B2 | 4/2003 | Hooven | |
| 6,558,375 B1 | 5/2003 | Sinofsky et al. | |
| 6,558,382 B2 | 5/2003 | Jahns et al. | |
| 6,572,609 B1 | 6/2003 | Farr et al. | |
| 6,579,285 B2 | 6/2003 | Sinofsky | |
| 6,599,288 B2 * | 7/2003 | Maguire et al. | 606/27 |
| 6,663,622 B1 | 12/2003 | Foley et al. | |
| 6,736,808 B1 * | 5/2004 | Motamedi et al. | 606/15 |
| 6,743,225 B2 * | 6/2004 | Sanchez et al. | 606/34 |
| 6,802,840 B2 | 10/2004 | Chin et al. | |
| 6,805,128 B1 | 10/2004 | Pless et al. | |
| 6,805,129 B1 | 10/2004 | Pless et al. | |
| 6,811,562 B1 | 11/2004 | Pless | |
| 6,817,999 B2 | 11/2004 | Berube et al. | |
| 6,899,710 B2 | 5/2005 | Hooven | |
| 6,949,095 B2 * | 9/2005 | Vaska et al. | 606/41 |
| 6,953,457 B2 | 10/2005 | Farr et al. | |
| 6,971,394 B2 | 12/2005 | Sliwa, Jr. et al. | |
| 2002/0022829 A1 | 2/2002 | Nagase et al. | |
| 2002/0052621 A1 * | 5/2002 | Fried et al. | 606/192 |
| 2002/0068924 A1 | 6/2002 | Sinofsky | |
| 2002/0087151 A1 | 7/2002 | Mody et al. | |
| 2002/0100485 A1 * | 8/2002 | Stevens et al. | 128/898 |
| 2002/0128636 A1 | 9/2002 | Chin et al. | |
| 2002/0193782 A1 | 12/2002 | Ellis et al. | |
| 2003/0023236 A1 * | 1/2003 | Gowda et al. | 606/15 |
| 2003/0029462 A1 | 2/2003 | Cox et al. | |
| 2003/0050630 A1 | 3/2003 | Mody et al. | |
| 2003/0050631 A1 | 3/2003 | Mody et al. | |
| 2003/0060813 A1 | 3/2003 | Loeb et al. | |
| 2003/0069575 A1 | 4/2003 | Chin et al. | |
| 2003/0069577 A1 | 4/2003 | Vaska et al. | |
| 2003/0078566 A1 | 4/2003 | Elliott et al. | |
| 2003/0083654 A1 | 5/2003 | Chin et al. | |
| 2003/0109868 A1 | 6/2003 | Chin et al. | |
| 2003/0120268 A1 * | 6/2003 | Bertolero et al. | 606/32 |
| 2003/0125730 A1 | 7/2003 | Berube et al. | |
| 2003/0163128 A1 | 8/2003 | Patil et al. | |
| 2003/0195496 A1 * | 10/2003 | Maguire et al. | 606/27 |
| 2003/0199860 A1 | 10/2003 | Loeb et al. | |
| 2003/0220639 A1 | 11/2003 | Chapelon et al. | |
| 2004/0006333 A1 | 1/2004 | Arnold et al. | |
| 2004/0019348 A1 * | 1/2004 | Stevens et al. | 606/34 |
| 2004/0054363 A1 | 3/2004 | Vaska et al. | |
| 2004/0092913 A1 | 5/2004 | Hennings et al. | |
| 2004/0102771 A1 | 5/2004 | Bertolero et al. | |
| 2004/0143257 A1 | 7/2004 | Fuimaono | |
| 2004/0147912 A1 | 7/2004 | Sinofsky | |
| 2004/0147913 A1 | 7/2004 | Sinofsky | |
| 2004/0199151 A1 | 10/2004 | Neuberger | |
| 2004/0260278 A1 | 12/2004 | Anderson et al. | |
| 2005/0075629 A1 | 4/2005 | Chapelon et al. | |
| 2005/0096643 A1 | 5/2005 | Brucker et al. | |
| 2005/0182392 A1 | 8/2005 | Brucker et al. | |
| 2005/0209589 A1 | 9/2005 | Berman et al. | |
| 2005/0273090 A1 | 12/2005 | Nieman et al. | |
| 2006/0009759 A1 | 1/2006 | Chrisitian et al. | |
| 2006/0025762 A1 | 2/2006 | Mohan et al. | |
| 2006/0084960 A1 | 4/2006 | Mester et al. | |

FOREIGN PATENT DOCUMENTS

| | | |
|---|---|---|
| WO | WO 96/34569 | 11/1996 |
| WO | WO 01/03599 A2 | 1/2001 |
| WO | WO 01/58373 A1 | 8/2001 |
| WO | WO 2006/050011 A1 | 5/2006 |
| WO | WO 2007/109246 A2 | 9/2007 |

OTHER PUBLICATIONS

Chiappini, et al., "Cox/Maze III Operation Versus Radiofrequency Ablation for the Surgical Treatment of Atrial Fibrillation: A Comparative Study," *Ann. Thorac. Surg.*, No. 77, pp. 87-92 (2004).

Cox, "Atrial fibrillation II: Rationale for surgical treatment," *The Journal of Thoracic and Cardiovascular Surgery.*, vol. 126, No. 6, pp. 1693-1699 (2003).

Fried, N. et al., "Linear Lesions in Myocardium Created by Nd:YAG Laser Using Diffusing Optical Fibers: In Vitro and In Vivo Results," *Lasers in Surgery and Medicine*, vol. 27, pp. 295-304 (2000).

Keane, D. et al., "Linear Atrial Ablation With a Diode Laser and Fiberoptic Catheter," *Circulation*, vol. 100, e59-e60 (1999).

Kubota, H. et al., "Atrial Ablation With an IRK-151 Infrared Coagulator," *Ann. Thorac. Surg.*, vol. 66, pp. 95-100 (1998).

Thomas, S. et al., Production of Narrow but Deep Lesions Suitable for Ablation of Atrial Fibrillation Using a Saline-Cooled Narrow Beam Nd:YAG Laser Catheter, *Lasers in Surgery and Medicine*, vol. 38, pp. 375-380.

Viola et al., "The Technology in Use for the Surgical Ablation of Atrial Fibrillation," *Seminars in Thoracic and Cardiovascular Surgery*, vol. 14, No. 3, pp. 198-205 (2002).

Ware, D. et al., "Slow Intramural Heating With Diffused Laser Light: A Unique Method for Deep Myocardial Coagulation," *Circulation*, vol. 99, pp. 1630-1636 (Mar. 30, 1999).

Bruneval, P. et al., "Nd-YAG laser-induced injury in dog myocardium: optical and ultrastructural study of early lesions," *European Heart Journal*, vol. 8, pp. 785-792 (1987).

Curtis, A. et al., "Modification of Atrioventricular Conduction Using a Combined Laser-Electrode Catheter," *PACE*, vol. 17, Part I, pp. 337-348 (Mar. 1994).

Derbyshire, G. et al., "Thermally Induced Optical Property Changes in Myocardium at 1.06 μm," *Lasers in Surgery and Medicine*, vol. 10, pp. 28-34 (1990).

Fuller, I. et al., "Intramural Coronary Vasculature Prevents Transmural Radiofrequency Lesion Formation. Implications for Linear Ablation," *Circulation*, vol. 107, pp. 1797-1803 (Apr. 2003).

Hindricks, G. et al., "Percutaneous endocardial application of Nd-YAG laser energy: an experimental feasibility study for ablation of ventricular myocardium," *Z. Kardiol*, vol. 80, pp. 673-680 (1991) (Summary in English).

Hiaro, K. et al., "Transcatheter Neodymium-Yttrium-Aluminum-Garnet Laser Coagulation of Canine Ventricle Using a Balloon-Tipped Cardioscope," *Japanese Circulation Journal*, vol. 61, pp. 695-703 (Aug. 1997).

Inoue, Y. et al., "Feasibility Study of Vascular-Endoscopic Valvuloplasty. Using a Laser and Flexible Endoscope," *ASAIO Journal*, vol. 40, pp. M811-M815 (1994).

Ischinger, T. et al., "The use of thermal laser action for cardiovascular recanalization; an example of Nd:YAG laser," *Z. Kardiol*, vol. 8, pp. 689-700 (1989) (Summary in English).

Littmann, L. et al., "Catherization Technique for Laser Photoablation of Atrioventricular Conduction from the Aortic Root in Dogs," *PACE*, vol. 16, Part I, pp. 401-406 (Mar. 1993).

Littmann, L. et al., "Neodymium:YAG Contact Laser Photocoagulation of the In Vivo Canine Epicardium: Dosimetry, Effects of Various Lasing Modes, and Histology," *Lasers in Surgery and Medicine*, vol. 13, pp. 158-167 (1993).

Menz, V. et al., "Linear Lesion Formation by ND:YAG Laser Versus Radiofrequency Energy in Porcine Atria," *PACE*, vol. 23, Part II, pp. 1848-1851 (Nov. 2000).

Obelienius, V. et al., "Histological Studies of Myocardium Zones Irradiated with Nd-YAG Laser," *Lasers in Surgery and Medicine*, vol. 5, pp. 475-483 (1985), vol. 5, pp. 475-483 (1985).

Obelienius, V. et al., "Transvenous Ablation of the Atrioventricular Conduction System by Laser Irradiation Under Endoscopic Control," *Lasers in Surgery and Medicine*, vol. 5, pp. 469-474 (1985).

Ogura, M. et al., "Myocardium Tissue Ablation with High-Peak-Power Nanosecond 1,064- and 532-nm Pulsed Lasers: Influence of Laser-Induced Plasma," *Lasers in Surgery and Medicine*, vol. 31, pp. 136-141 (2002).

Ohtake, H. et al., "Myocardial Coagulation by Intraoperative Nd:YAG Laser Ablation and its Dependence on Blood Perfusion," *PACE*, vol. 17, pp. 1627-1631 (Oct. 1994).

Schuger, C. et al., "Percutaneous Transcatheter Laser Balloon Ablation from the Canine Coronary Sinus: Implications for the Wolff-Parkinson-White Syndrome," *Lasers in Surgery and Medicine*, vol. 10, pp. 140-148 (1990).

Selle, J. et al., "Successful Clinical Laser Ablation of Ventricular Tachycardia: A Promising New Therapeutic Method," *Ann. Thorac. Surg.*, vol. 42, No. 4, pp. 380-384 (Oct. 1986).

Selle, J. et al., "Laser Ablation of Ventricular Tachycardia," *Thorac. Cardiovasc. Surgeon*, vol. 36, pp. 155-158 (Special Issue) (1988).

Splinter, R. et al., "Optical Properties of Normal, Diseased, and Laser Photocoagulated Myocardium at the Nd:YAG Wavelength," *Lasers in Surgery and Medicine*, vol. 11, pp. 117-124 (1991).

Splinter, R. et al., "Ultrasonic Characterization of Myocardial Photocoagulation Lesion Size in Vivo During Nd:YAG Laser Irradiation," *J. Clin. Ultrasound*, vol. 22, No. 4, pp. 221-229 (May 1994).

Svenson, R. et al., "Neodymium: YAG laser photocoagulation: a successful new map-guided technique for the intraoperative ablation of ventricular tachycardia," *Circulation*, vol. 76, No. 6, pp. 1319-1328 (Dec. 1987).

Svenson, et al., "Regional Atrial Electrical Isolation. Lines of Block Created By Laser Photocoagulation: A Possible Intraoperative Approach To Atrial Fibrillation", *PACE*, vol. 22, p. 774 (Abstract) (Apr. 1999).

van Brakel, T. et al., "Evaluation of Epicardial Microwave Ablation Lesions: Histology Versus Electrophysiology," *Ann. Thorac. Surg.*, vol. 78, pp. 1397-1402 (2004).

"Vascu-Statt® Single-Use Bulldog Clamps," Scanlan International, http://www.scanlaninternational.com/singleuse/vascustatt.asp, 1 page (Copyright 2004).

Verdaasdonk, R. et al., "Explosive onset of continuous wave laser tissue ablation." *Phys. Med. Biol.*, vol. 35, No. 8, pp. 1129-1144 (1990).

Wagshall, et al., "A Novel Catheter Design For Laser Photocoagulation Of The Myocardium To Ablate Ventricular Tachycardia", *Journal of Interventional Cardiac Electrophysiology*, Aug. 7(1), pp. 13-22 (2002).

Weber, H. et al., "Percutaneous Nd:YAG Laser Coagulation of Ventricular Myocardium in Dogs Using a Special Electrode Laser Catheter," *PACE*, vol. 12, pp. 899-910 (Jun. 1989).

Weber, H. et al., "Effects of Nd:YAG Laser Coagulation of Myocardium on Coronary Vessels," *Lasers in Surgery and Medicine*, vol. 10, pp. 133-139 (1990).

Weber, H. et al., "Catheter-directed laser coagulation of atrial myocardium in dogs," *European Heart Journal*, vol. 15, pp. 971-980 (1994).

Weber, H. et al., "Laser catheter ablation of atrial flutter and of atrioventricular nodal reentrant tachycardia in a single session," *European Heart Journal*, vol. 15, pp. 1147-1149 (1994).

Weber, H. et al., "Mapping Guided Laser Catheter Ablation of the Atrioventricular Conduction in Dogs," *PACE*, vol. 19, pp. 176-187 (Feb. 1996).

Weber, H. et al., "Laser catheter coagulation of atrial mycoardium for ablation of atrioventricular nodal reentrant tachycardia. First clinical experience," *European Heart Journal*, vol. 18, pp. 487-495 (1997).

Weber, H. et al., "Laser verus Radiofrequcney Catheter Ablation of Ventricular Myocardium in Dogs: A Comparative Test," *Cardiology*, vol. 88, pp. 346-352 (1997).

Weber, H. et al., "Laser Catheter Coagulation of Normal and Scarred Ventricular Myocardium in Dogs," *Lasers in Surgery and Medicine*, vol. 22, pp. 109-119 (1998).

Wietholt, D. et al., "Nd:YAG Laser-Photocoagulation: Acute Electrophysiological, Hemodynamic, and Morphological Effects in Large Irradiated Areas," *PACE*, vol. 15, pp. 52-59 (Jan. 1992).

\* cited by examiner

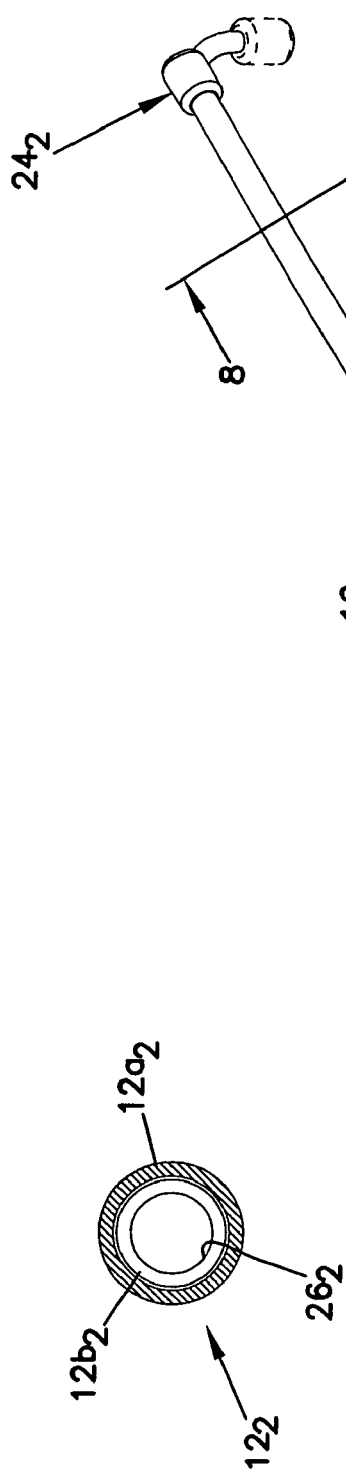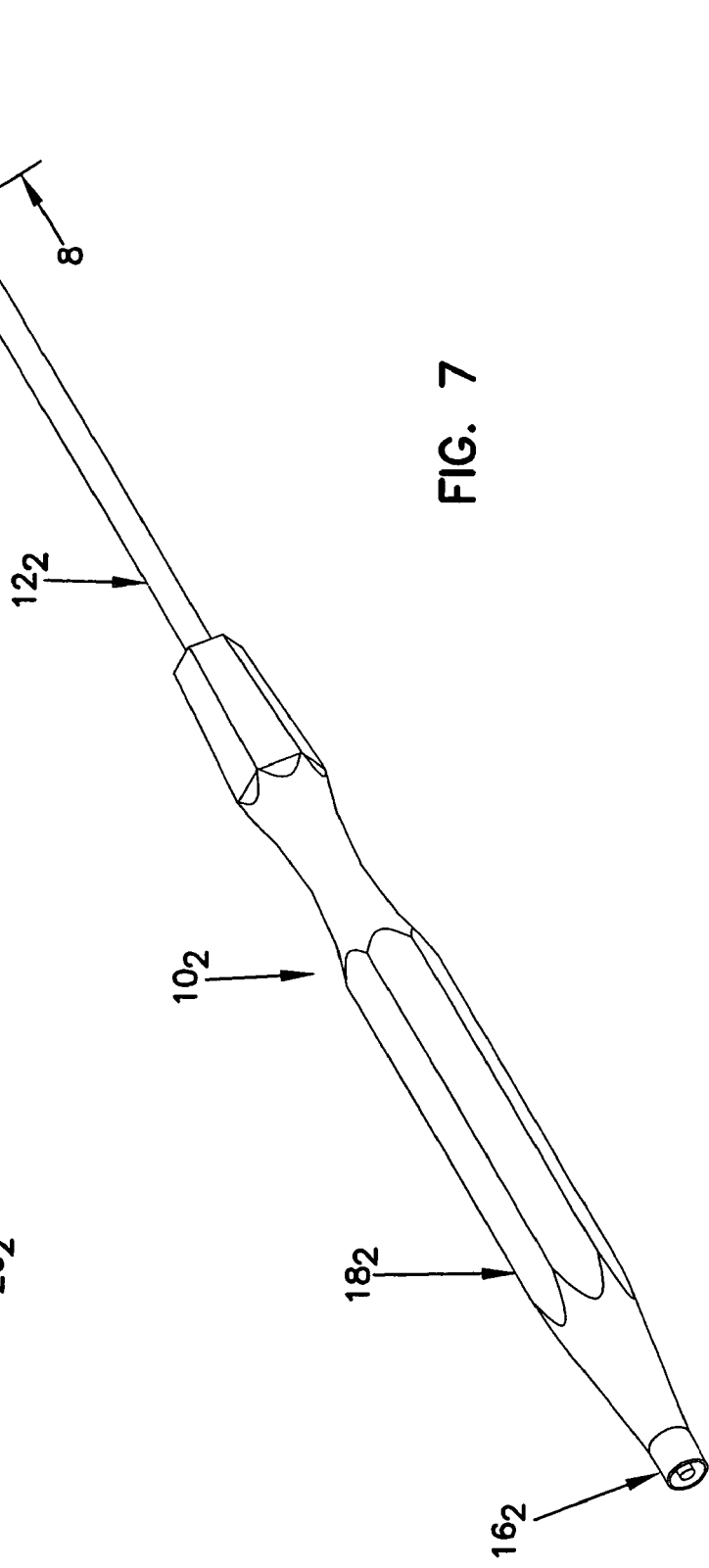

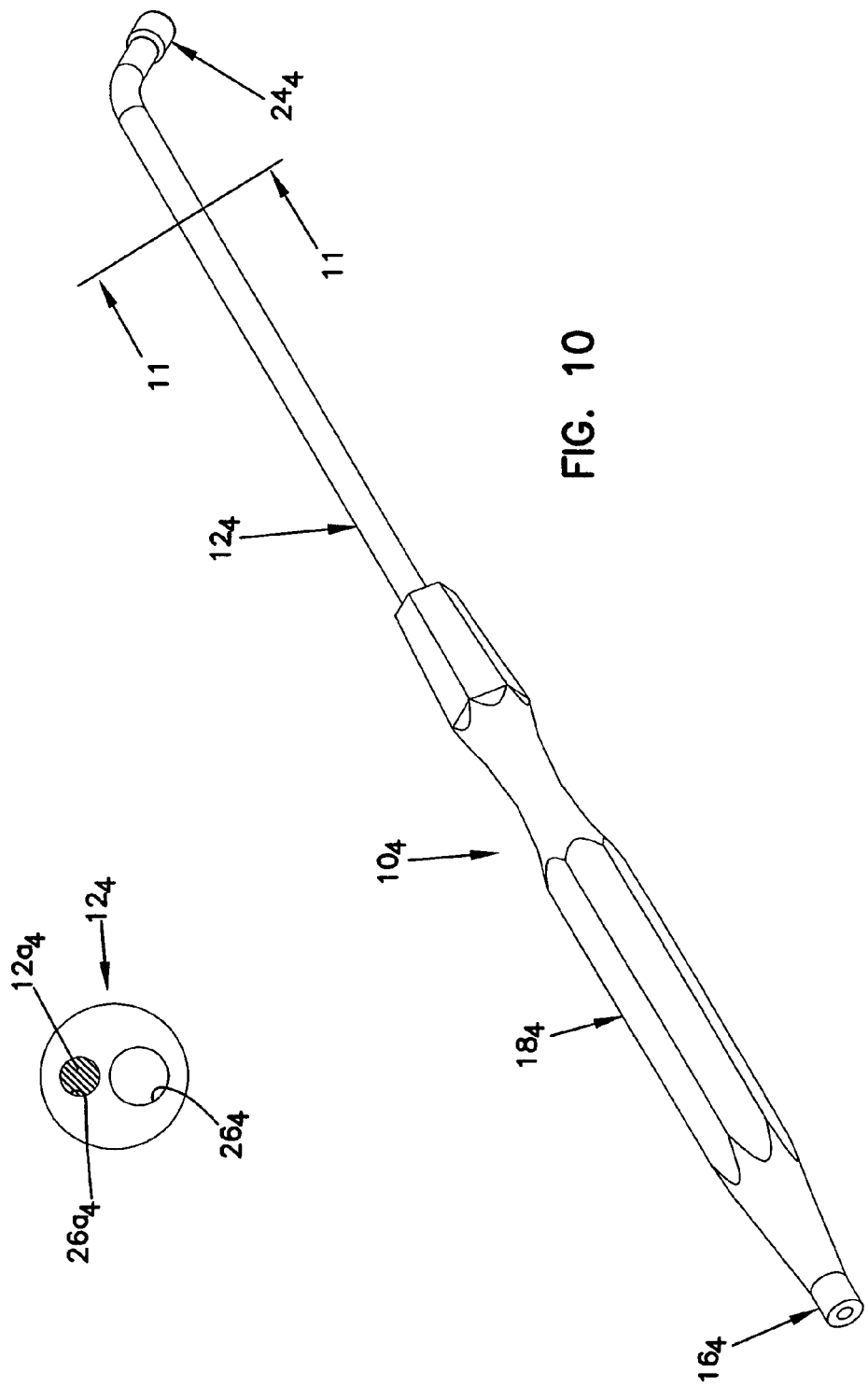

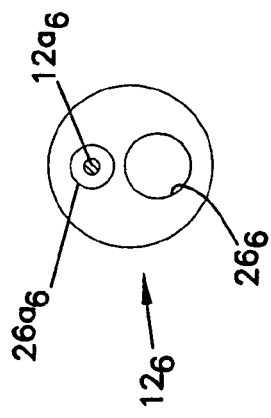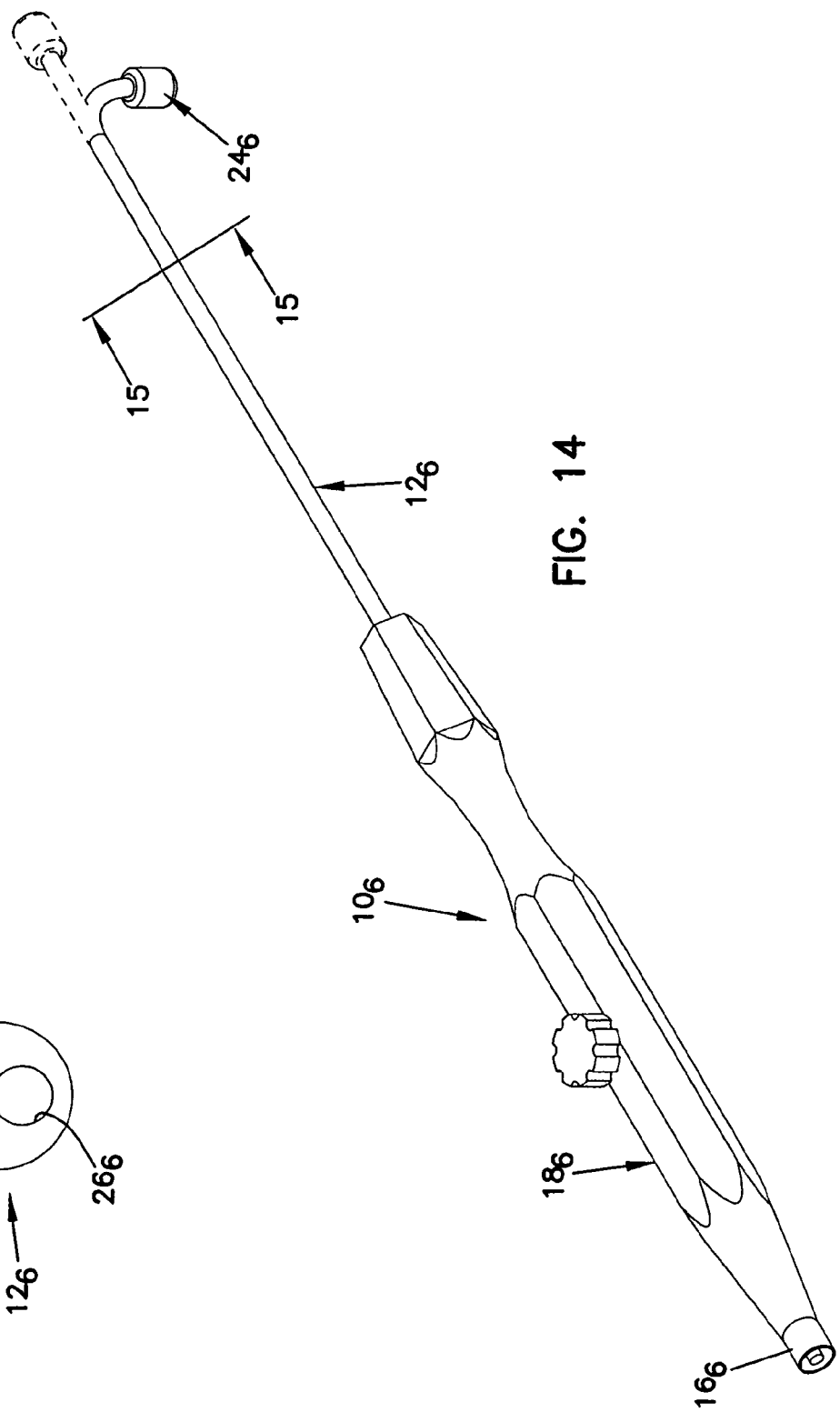

CARDIAC LESIONS WITH CONTINUITY TESTING

CROSS-REFERENCE TO RELATED APPLICATION

This patent application is a continuation application of commonly assigned and copending U.S. patent application Ser. No. 10/975,674 filed Oct. 28, 2004 and which claims priority to U.S. Provisional Patent Application Ser. No. 60/516,242 with an assigned filing date of Oct. 3, 2003 and filed in the names of Gregory G. Brucker and Robert H. Svenson.

BACKGROUND OF THE INVENTION

1. Field of the Invention

The present invention relates to surgical instruments for laser cardiac ablation procedures. More particularly, the invention relates to a wand including a fiber optic transmission channel for atrial cardiac ablation.

2. Description of the Prior Art

A. Atrial Fibrillation

It is known that at least some forms of cardiac arrhythmia are caused by electrical impulses traveling through the cardiac muscle tissue by abnormal routes. In a normal, non-arrhythmic heart, electrical nerve impulses travel in an orderly and well-defined fashion through the sinoatrial node and then through the atrioventricular node in order to create an orderly flow of nerve impulses that lead to contraction in the heart.

In cardiac arrhythmia, cardiac impulses travel disorderly and undesirable paths through the cardiac tissue leading to disorderly and inefficient contraction of heart muscle. These fibrillations prevent the heart from pumping blood efficiently and can lead to death.

B. Maze Procedure—Generally

One technique for treating atrial fibrillation is to surgically create lines in the heart muscle tissue (myocardium) whereby electrical conduction of nerve impulses is blocked or rerouted. This technique for creating lines of electrical blockage is referred to as the Maze procedure.

Initial approaches to performing the Maze procedure involved invasive surgery in which a series of linear incisions are made in the cardiac tissue and then sutured together. The lines of scar tissue that form in the incisions do not conduct nerve impulses and are intended to prevent disorderly contraction of the atrial tissue.

In a typical Maze procedure, up to six non-conductive lines are required. Each of the non-conductive lines is typically several centimeters in length. Once these lines scar and heal, they disrupt electrical pathways that may support atrial fibrillation. Examples of the Maze procedure and other surgical techniques for treating atrial fibrillation are described in Chiappini, et al., "Cox/Maze III Operation Versus Radiofrequency Ablation for the Surgical Treatment of Atrial Fibrillation: A Comparison Study", *Ann. Thorac. Surg.*, No. 77, pp. 87-92 (2004) and Cox, "Atrial fibrillation II: Rationale for surgical treatment", *J. Thoracic and Cardiovascular Surg.*, Vol. 126, No. 6, pp. 1693-1699 (2003).

C. Less Invasive Maze Procedure Technologies

Less invasive ablation techniques have also been utilized to perform the Maze procedure. In such techniques, the surgeon typically drags an electrode in a linear fashion along the endocardial (internal) or epicardial (external) surface to produce a series of focal lesions. The scaring created by the focal lesions is hopefully contiguous and non-conductive of electrical impulses. For endocardial use, standard ablation catheters or catheters with extended distal electrodes are employed. Epicardially, specially designed handheld probes with a distal electrode for the application of ablating energy are often used.

For the greatest likelihood of success in a Maze procedure, it is particularly important that the lesions created be transmural. A transmural lesion extends through the full wall thickness of the cardiac muscle at the location of the lesion. One factor that obstructs obtaining transmural lesions from an epicardial approach of the heart is the cooling effect of blood in and around the heart. This is a particular difficulty when radio frequency (RF) energy is employed. The application of RF energy relies exclusively on thermal diffusion to create transmural lesions. The cooling effect of blood within the atrium tends to limit the depth to which thermal lesions can be formed.

It is desirable to create a full thickness transmural lesion but undesirable to perforate the atrial wall. Perforation of the atrial wall leads to a weakening of the heart structure as well as significant bleeding during surgery that must be controlled.

Additionally, producing transmural lesions with RF energy tends to heat the surface tissue at the point of probe contact this. This tends to create burns and adhesion between the probe and the heart tissue. Such adhesions can insulate the probe from the heart tissue blocking the efficient application of energy. These procedures are also a problem for the surgeon and staff who often must stop to clean the tip of the probe.

A discussion of techniques and technologies for treating atrial fibrillation is set forth in Viola, et al., "The Technology in Use for the Surgical Ablation of Atrial Fibrillation", *Seminars in Thoracic and Cardiovascular Surgery*, Vol. 14, No. 3, pp. 198-205 (2002). Viola et al. describe numerous ablation technologies for treating atrial fibrillation with the Maze procedure. These include cryosurgery, microwave energy, radiofrequency energy, and laser ablation.

D. Laser Ablation and the Maze Procedure i. Treatment of Atrial Fibrillation with Laser Energy The use of lasers in treating atrial fibrillation is desirable. Laser ablation is fast and the resulting lesion is narrow. Viola, et al., "The Technology in Use for the Surgical Ablation of Atrial Fibrillation", *Seminars in Thoracic and Cardiovascular Surgery*, Vol. 14, No. 3, pp. 201, 204 (2002). However, in the prior art, laser ablation for treating atrial fibrillation has been troublesome.

Viola et al. discuss problems associated with the use of laser energy to treat atrial fibrillation. These concerns are directed to safety and reliability and note that lasers are prone to overheating because of the absence of a self-limiting mechanism. The authors note that over-heating with lasers can lead to crater formation and eventually to perforation, especially when using pin-tip devices. Viola, et al., sutara, at p. 203. The authors note that the high power of laser ablation (described as 30 to 80 Watts) results in the laser technique not being widely clinically applied. Id., at p. 201. The mechanical effects resulting from direct heating of the myocardial tissue with laser energy results in cellular explosions caused by shock waves. Viola, et al., supra, at p. 201.

The possibility for perforation of the myocardium with laser energy raises a particular concern for treating atrial fibrillation. The myocardial wall of the atria is quite thin (e.g., about 2 mm in thickness in some locations). A coring of the myocardium by a laser could result in a full wall thickness perforation and resulting leakage of blood.

Viola et al. note the development of a long probe laser that allows diffusion of the laser thermal energy over the long probe tip in a unidirectional fashion. Id., at p. 201. While not mentioning the source of this long probe tip, it is believed by the present inventors to be referring to the atrial fibrillation laser of CardioFocus, Inc., Norton, Mass. (USA) as described in U.S. Patent Application Publication No. 2004/6333A1 in the name of Arnold, et al. (published Jan. 8, 2004) and U.S. Pat. No. 6,579,285 issued to Sinosky. Unfortunately, this technology defocuses energy and increases the risk (particularly on a beating heart) of creating a lesion that is less than transmural.

ii. Inapplicability of Ventricular Laser Treatment

Lasers have been effectively used for treating ventricular tachycardia. An example of such is described in U.S. Pat. No. 5,104,393 to Isner et al. dated Apr. 14, 1992.

Unfortunately, while such laser treatments are appropriate for treating the left ventricle. They are not applicable to treating the atria.

The myocardial wall of the left ventricle is substantially thicker than the atria. Therefore, perforation risks are less. Also, in a ventricular treatment, the laser is targeted against a tissue area for substantial periods of time (e.g., about two minutes). To accomplish this, the lasers have a fixation member at the laser tip. (see, e.g., element 42 in the '393 patent). The lasers may also be provided with a temperature sensing tip as described in U.S. Pat. No. 5,830,209 to Savage et al. dated Nov. 3, 1998. Temperature probes provide a temperature profile at the tissue treatment site. U.S. Pat. No. 5,827,267 to Savage et al. dated Oct. 27, 1998 teaches a multi-fiber laser with recirculating coolant contained by a quartz lens and a 50 to 100 watt power source with irradiation up to ten minutes.

The aforementioned lasers are catheter delivered to project laser energy to the interior (endocardial) surface of the heart in the ventricle. In treating tachycardia as described, the laser is intended to create a lesion of necrosed tissue at a discrete target site. To accomplish this, a high power laser is provided with an anchor or fixation device to hold the laser tip at the target site for a prolonged period of laser irradiation.

Ventricular treatment lasers are not applicable to treating atrial fibrillation. In treating atrial fibrillation, a long, narrow, transmural lesion is desired to be formed in a pathway consistent with the Maze procedure. The high power laser of the ventricular treatment lasers presents risk of damage and perforation of the thin-walled atrium as noted by Viola, et al. Further, the single-point treatment of ventricular lasers (created with the assistance of myocardial fixation) is inappropriate to the objectives of the Maze procedure and the tips of such lasers are not optimized for atraumatic movement over the epicardial surface of the atria.

In the foregoing, applicants have referred to the use of lasers in atrial fibrillation as "ablation" techniques. While the use of the term "ablation" is a common usage when describing atrial fibrillation treatments, such usage is an unfortunate misnomer. In treating atrial fibrillation, there is no intent or desire to ablate tissue to the extent that term implies removal of tissue. In fact, in a strict sense, ablation is to be avoided. As noted in Viola et al, it is undesirable to create perforations through laser ablation. Instead, the desire is to create a full myocardial wall thickness (i.e., "transmural") lesion of scar tissue or necrosed myocardial tissue which is narrow and remains in situ in the surrounding myocardium to act as a barrier to undesirable transmission of electrical or neural impulses through the myocardium.

In the strict sense of tissue removal, ablation lasers have been used in the ventricle in transmyocardial revascularization ("TMR") procedures. In TMR procedures, the object is to form a bore from the left ventricle partially through the myocardium with the hope the bore will facilitate the flow of oxygenated blood into ischemic myocardial tissue. Of course, such technology is not applicable to atrial fibrillation treatments were bore formation (or perforations) are to be avoided.

In all types of laser treatments or RF electrode treatments, it is important that the apparatus not damage the tissue through mechanical damage. In ventricular lasers, the traumatic tip does not risk damage to the endocardial tissue since it is immobilized in place with an anchor or fixation as described in the afore-mentioned U.S. Pat. No. 5,104,393. In the afore-mentioned U.S. Patent Application Publication No. 2004/6333A1, such risks are minimized by laying the diffusing probe over the tissue area.

In the present invention, it is contemplated to draw the tip of a laser wand over the surface of the heart in the region of the atria. In doing so, care must be taken to minimize risk of injury to the atria. For example, the atria are very thin walled. Also, while not as abundant in the atria as in the ventricle region, superficial blood vessels reside on the epicardial surface. A moving object should minimize snags or tears.

From the above, while laser treatment of atrial fibrillation is desirable, existing technology has been inadequate. It is an object of the present invention to provide an apparatus and method for treating atrial fibrillation with the benefits of a laser treatment. The surgical art would benefit from a laser probe for creating transmural, non-perforating lesions without the problems of sticking or snagging on the atrial wall tissue. Further, it is desirable that the probe itself not heat up and that energy be efficiently applied to the heart tissue.

E. Conductivity Verification

A further difficulty with creating linear nonconductive lesions is the inability to verify that a truly nonconductive lesion has been produced. If a transmural lesion is not properly formed in accordance with the Maze procedure, the treatment for atrial fibrillation may not be successful. This could require a second surgical procedure. It would be helpful if the surgeon could promptly discern whether a particular linear lesion is truly non-conducting at the time of the original procedure to permit correction at that time. This would enable prompt re-treatment if necessary.

F. Additional Cardiac Ablation Technology

A large variety of devices for cardiac ablation exist in the art. Devices for cardiac ablation combining electrodes and laser include: U.S. Pat. No. 4,785,815 issued to Donald Cohen, U.S. Pat. No. 5,172,699 issued to Robert Svenson et al, U.S. Pat. No. 5,306,274 issued to Gary Long. U.S. Pat. No. 5,769,843 issued to George Abela et al, U.S. Pat. No. 5,824,005 issued to Massoud Motamedi et al, U.S. Pat. No. 6,024,739 issued to Dean Ponzi et al and U.S. Pat. No. 6,200,310 B1 issued to Shlomo Ben-Haim et al.

Devices for cardiac ablation including electrodes but no laser include: U.S. Pat. No. 5,354,296 issued to David Turkel, U.S. Pat. No. 6,063,081 issued to Peter Mulier et al., U.S. Pat. No. 6,161,543 issued to James Cox et al., and U.S. Pat. No. 6,231,518 B1 issued to James Grabek et al.

Device employing laser for cardiac ablation include: U.S. Pat. No. 4,693,244 to Daikuzono, U.S. Pat. Nos. 4,985,028 and 5,104,393 to Jeffrey Isner et al., U.S. Pat. No. 5,282,798 issued to Bruse et al., U.S. Pat. No. 4,955,267 issued to Jacobs, et al., U.S. Pat. No. 5,389,096 issued to Michael Aita et al., U.S. Pat. No. 5,897,551 issued to Everett, et al., U.S.

Pat. No. 5,951,541 issued to Simpson, et al., U.S. Pat. No. 6,066,131 issued to Richard Mueller et al., U.S. Pat. No. 6,110,167 issued to Cozean, et al., U.S. Pat. No. 6,135,996 issued to Kolesa et al., U.S. Pat. No. 4,693,244 issued to Daikuzuno, U.S. Pat. No. 5,046,810 issued to Steiner et al and U.S. Pat. No. 5,534,000 issued to Bruce.

Devices for intracardiac use as catheters include: U.S. Pat. No. 5,782,828 issued to Peter Chen, U.S. Pat. No. 5,800,428 issued to Dale Nelson et al and U.S. Pat. No. 6,063,080 issued to Dale Nelson et al.

Devices for epicardial procedures include: U.S. Pat. Nos. 5,380,316 and 5,925,033 issued to Michael Aita et al., U.S. Pat. No. 5,728,091 also issued to Sam Payne et al, U.S. Pat. No. 6,231,568 B1 issued to Marvin P. Loeb et al, U.S. Pat. No. 6,237,605 B1 issued to Matthias Vaska et al.

SUMMARY OF THE INVENTION

According to a preferred embodiment of the present invention, a method and apparatus are disclosed for treating a body tissue in situ (e.g., an atrial tissue of a heart to treat) atrial fibrillation. The method and apparatus include identifying a patient with atrial fibrillation and accessing a surface of the tissue. A lesion formation tool is positioned against the accessed surface. The tool includes an optical fiber for guiding a coherent waveform of a selected wavelength to a fiber tip for discharge of light energy from the fiber tip. The wavelength is selected for the light energy to penetrate a full thickness of the tissue to form a volume of necrosed tissue through the thickness of the tissue. The tool further includes a guide tip coupled to the fiber tip. The guide tip is adapted to have a discharge bore aligned with the fiber tip to define an unobstructed light pathway from the fiber tip to the tissue surface. The guide tip is further adapted to be placed against the tissue surface with the guide tip slidable along the tissue surface in atraumatic sliding engagement. The lesion formation tool is manipulated to draw the guide tip over the tissue surface in a pathway while maintaining the discharge bore opposing the tissue surface to form a transmural lesion in the tissue extending a length of the pathway.

In an alternate embodiment, an operator can manipulate an angle of the tool tip relative to a handle. In a still further embodiment, the tool has sensing electrodes to allow for immediate verification of the nonconductive nature of a lesion produced.

In a detailed preferred embodiment, the tool includes a fluid pathway for perfusing a liquid around the location where the lesion is created. The tool includes an optical fiber, a support assembly including a tubular shaft and handle, an internal lumen for a flushing fluid and an optical connector for interfacing to a laser. The tip assembly includes an optical fiber that couples the probe to a laser and transmits laser energy to the tip. Preferably the tip of the probe is shaped to allow for easy movement across the surface of the heart. In addition, the tip also spaces the fiber at a fixed position relative to the tissue surface to optimize achievement of transmural lesions without perforation of the tissue.

BRIEF DESCRIPTION OF THE DRAWINGS

FIG. 7 is a view similar to FIG. 6 and showing an alternative embodiment of adjustability feature;

FIG. 8 is a view taken along line 8-8 of FIG. 7;

FIG. 10 is the view of FIG. 6 showing a yet further alternative embodiment of an adjustability feature;

FIG. 11 is a view taken along line 11-11 of FIG. 10;

FIG. 14 is the view of FIG. 6 showing a still further embodiment of an adjustability feature;

FIG. 15 is the view taken along line 15-15 of FIG. 14;

DETAILED DESCRIPTION OF THE PREFERRED EMBODIMENTS

Figure 1:
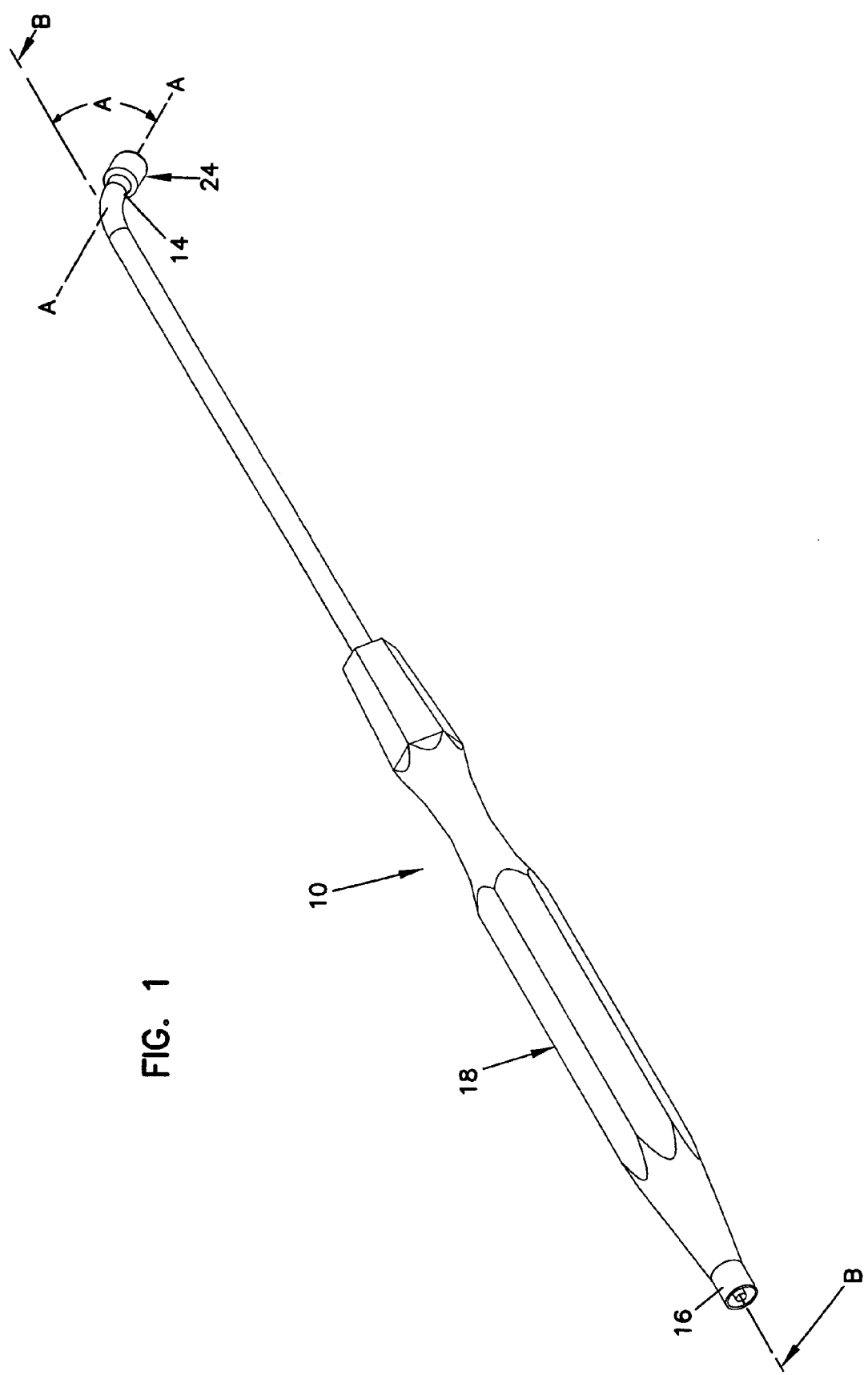
FIG. 1 is a top, right side and distal end perspective view of a laser surgical wand according to a first embodiment of the present invention.

Referring now to the drawing figures in which identical elements are numbered identically throughout, a description of a preferred embodiment of the present invention will now be provided. In the preferred embodiment, the invention is described as a lesion formation tool in the form of a surgical wand for applying laser energy to the epicardial surface of the heart to create a transmural ablation line along the heart. It will be appreciated that the atraumatic nature of the distal tip of the invention, as will be described, could also be used in a tool for creating such a line by applying the energy against the endocardial surface of the heart. As used in this application, the term "ablation" is used in the context of creating necrosed tissue in the myocardium while avoiding tissue perforation or removal.

Atraumatic Atrial Laser

Figure 2:
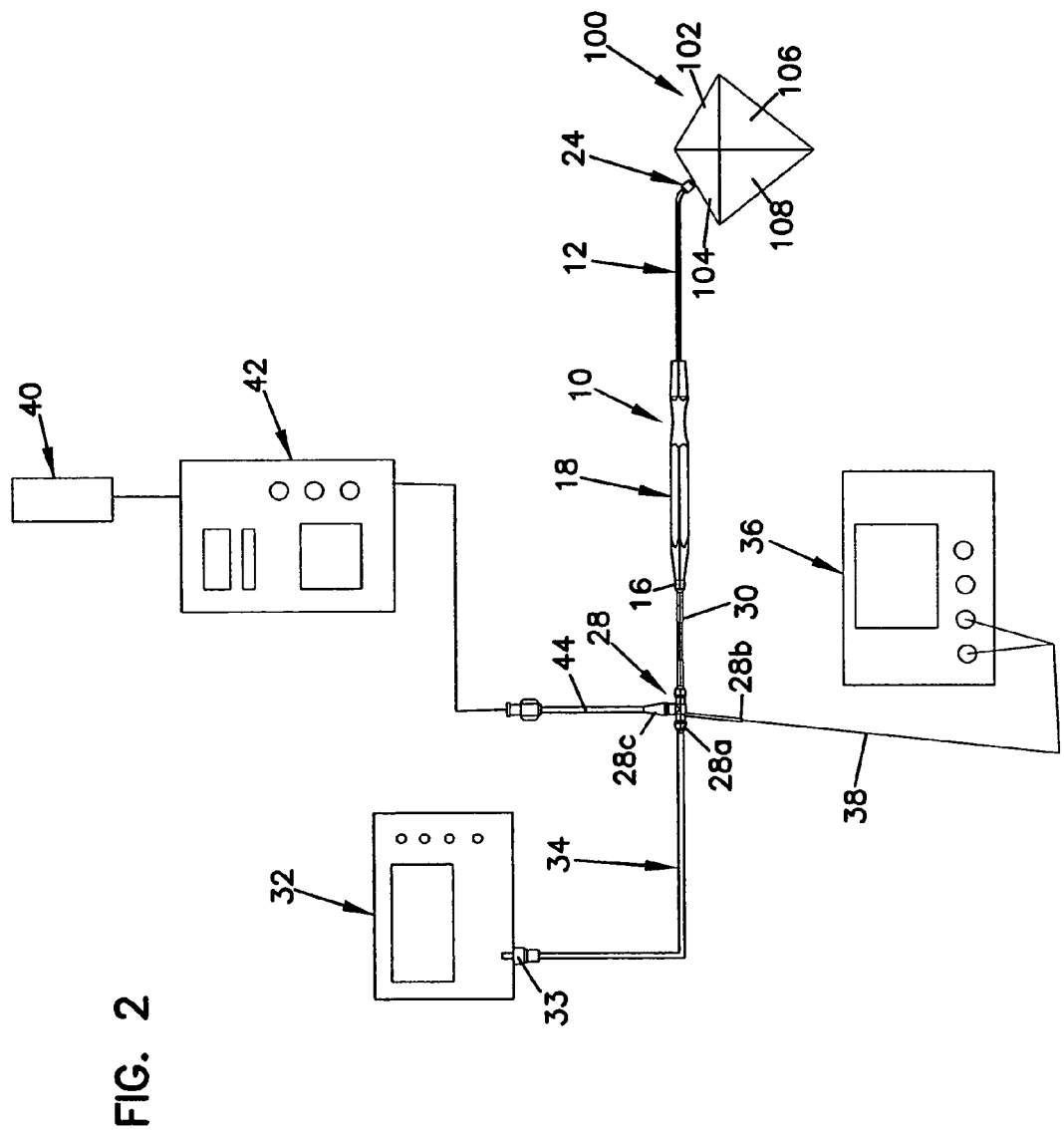
FIG. 2 is a schematic representation of the laser surgical wand of FIG. 1 connected to a laser energy source, a coolant fluid source and an optional monitoring apparatus.
Figure 3:
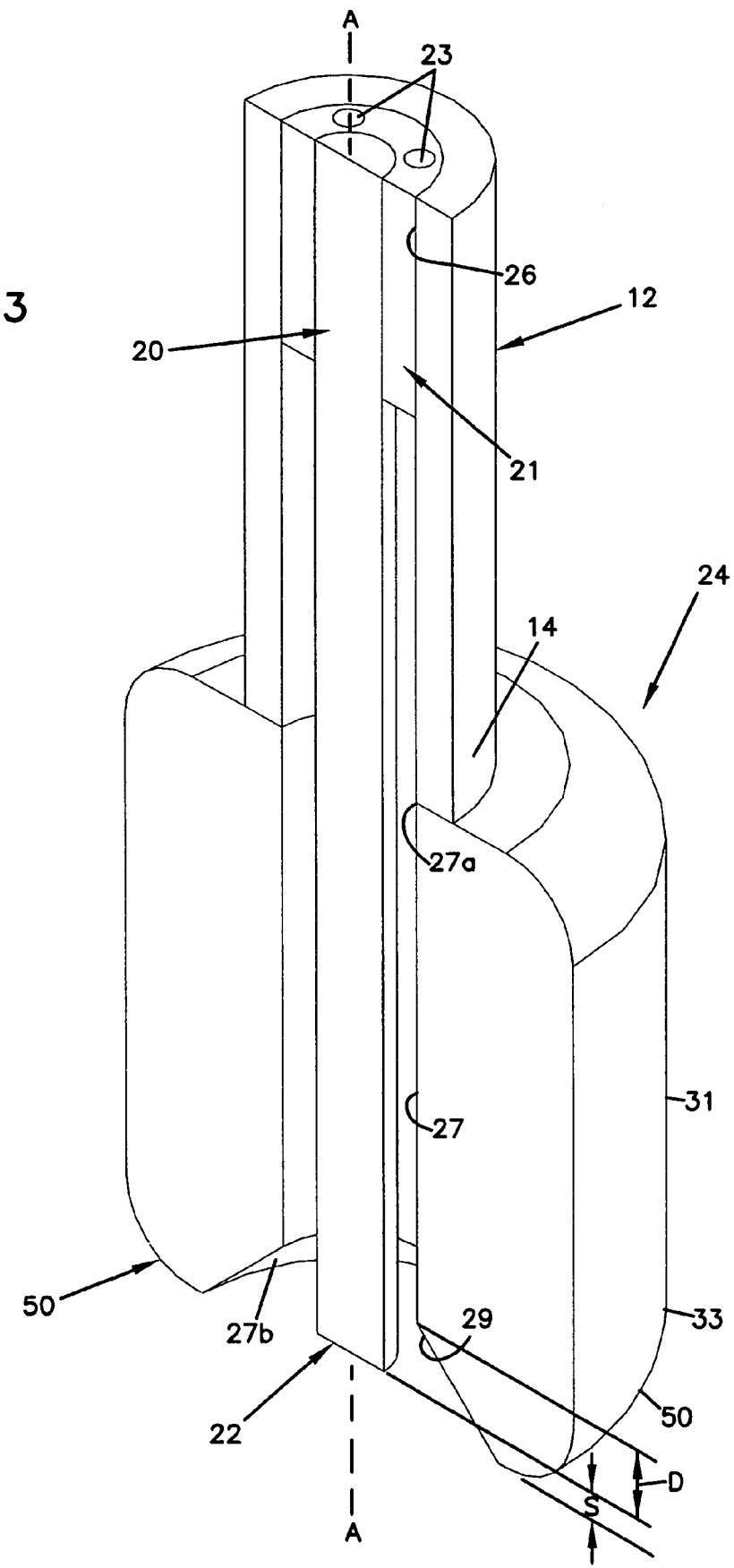
FIG. 3 is a perspective longitudinal section view of a distal tip of the wand of FIG. 1.

Referring first to FIGS. 1-3, a lesion formation tool is shown as a laser surgical wand 10 having an elongated shaft 12 with a distal end 14 and a proximal end 16. A handle 18 is carried on the shaft 12 at the proximal end 16. A guide tip 24 is connected to the distal end 14.

A waveguide in the form of an optical fiber 20 passes axially through the entire length of the shaft 12 and substantially though the entire length of the guide tip 24. The fiber 20 resides within aligned bores 26, 27 (FIG. 3) formed through the length of the shaft 12 and guide tip 24.

The fiber 20 is retained in the bores 26, 27 by a fixation collar 21 shown in cross-section in FIG. 3 (it will be appreciated the collar 21 is symmetrical about axis A-A). The collar 21 is a cylinder having an outer diameter sized to be snugly received within the bore 26 and an inner diameter to snugly receive the fiber 20. This collar 21 holds the fiber axis aligned with the axis of the shaft 12 and retains the fiber tip 22 the desired spacing from the distal edge of the guide tip 24 as will be described. A plurality of holes 23 are formed through the length of the collar 21 and permit fluid flow through the bores 26, 27 as will be described.

The fiber 20 (FIG. 3) terminates at a fiber tip (or discharge end) 22. The fiber tip 22 is cleaved or polished flat and perpendicular to the longitudinal axis A-A of the fiber 20. The aligned bores 26, 27 have internal diameters greater than the external diameter of the fiber with opposing surfaces of the fiber 20 and each of the shaft 12 and guide tip 24 defining an annular fluid passage surrounding the fiber 20 throughout its length.

FIG. 2 schematically illustrates the laser wand connected to supporting apparatus for use in treating atrial fibrillation. In FIG. 2, the heart 100 is shown schematically and divided into left and right atria 102, 104 and left and right ventricles 106, 108.

A coupling member 28 is connected to the proximal end 16 of the shaft 12 by a flexible connecting tubing 30. In FIG. 1, the tubing is shown severed at the proximal end 16. The tubing is an extrusion from the proximal end and has an internal diameter greater than the external diameter of the fiber 20. The tubing 30 acts to protect the fiber 20 from mechanical injury. Opposing surfaces of the tube 30 and optical fiber 20 define an extension of the fluid pathway 26 through the tubing 30.

A power source 32 (FIG. 2) is connected to the wand 10. The power source 32 is a laser energy source of the requisite wavelength and power for forming transmural lesions as will be described. A flexible tubing 34 connects the laser energy source 32 to a side 28a of the coupling member 28. The fiber 20 extends through the tubing 34 and is connected to the power source by a fiber optic connector 33.

FIG. 2 also shows an optional electrophysiology signal generator and monitor 36 connected via a cable to an electrical connector 28b of the coupling 28. Such coupling electrically connects the generator/monitor 36 to optional internal wires (not shown) of the wand 100 to optional electrodes carried on the guide tip 24. This optional feature will be discussed with reference to FIGS. 19 and 20.

Any wavelength suitable to create necrosed tissue in the myocardium without tissue removal could be used. In a preferred embodiment, the wavelength is a near-infrared wavelength selected to have a very low absorption and very high scatter in myocardial tissue. Biological tissue (such as the myocardium) is largely water. Wavelengths in the ranges of between about 470 to about 900 nanometers and between about 1050 to about 1150 nanometers are known to penetrate water with low absorption (e.g., less than about 30% absorption). *Lasers in Cardiovascular Medicine and Surgery: Fundamentals and Techniques*, George S. Abela, M.D., Editor, Kluwer Academic Publishers, 101 Philip Drive, Assinippi Park, Norwell, Mass. 02061 USA, p. 28 (1990). More preferably, the wavelength is selected from the ranges of 790 to 850 nanometers (which range corresponds to commercially available medical diode lasers) and 1050 to 1090 nanometers (which range corresponds to Nd:YAG lasers commonly used in other medical procedures). A laser energy source with a wavelength selected from these ranges will penetrate the full thickness of the myocardium and result in a transmural lesion (i.e., a fill-thickness necrosis of myocardial tissue in the atrium). Further such a wavelength minimizes carbonization of the tissue and perforation of the myocardial tissue. Such laser emissions are substantially coherent.

Only one wavelength need be passed through the fiber 20 to treat the tissue as described. Conveniently, this may be referred to as the therapeutic wavelength. The therapeutic wavelengths described are invisible to the human eye. It may also be desirable to concurrently pass a visible wavelength (the "targeting" wavelength) through the fiber 20 to permit an operator to visualize the precise location on the heart tissue being targeted by the therapeutic wavelength. With a targeting wavelength, if an operator holds the guide tip 24 at too great an angle to the heart surface, the visible light can escape the tip 24 giving the operator a visual signal that the tip 24 is at too great an angle.

The laser surgical wand 10 is also connected to a fluid source 40 which is a reservoir of a cooling fluid as will be described. An infusion fluid pump 42 urges fluid from the source 40 through a tubing 44 to a fluid inlet 28c of the coupling member 28. Therefore, the fluid is admitted to flow through the annular passages 26, 27 and discharge through the guide tip 24.

As will be more fully described, the fluid flow cools the material of the guide tip 24, washes biological material (e.g., blood, tissue debris or the like) from the light path between optical fiber 20 and the heart surface, and acts as a lubricant to further facilitate atraumatic gliding movement of the guide tip 24 over the surface of the heart.

The washing action of the fluid maximizes the laser energy impinging on the surface of the heart. Additionally, this fluid provides a means to cool the tissue in the region of the guide tip 24 to help ensure that tissue carbonization and subsequent vaporization of cardiac tissue do not occur. This substantially reduces the likelihood of perforation of the heart wall. Also, the fluid forms a protective layer at the discharge end 22 of optical fiber 20 which reduces the likelihood biological residue will impinge on and/or adhere to the discharge end 22 which can otherwise cause spalling of the fiber face 22 and reduce optical transmission of laser energy.

Since the fluid flows into the body of the patient, the fluid should be medical grade and biocompatible. Also, the fluid should have a low absorption of the laser energy. A preferred fluid is a physiological saline solution which may be supplied at ambient temperature.

The pump 42 includes control knobs and the like to permit an operator to set or modify a flow rate of the fluid. For example, an operator can set fluid flow as low as 0.2 milliliters per minute or as high as 20 milliliters per minute or any other desired setting. As will be described, some flow is preferred to cool the tip and wash the end of the fiber. For treating thin atrial tissue, the flow rate is preferably about 10 milliliters per minute which provides the afore-mentioned benefits but minimizes excessive fluid infusion into the patient.

In the description of FIG. 2, it will be appreciated that generator/monitors 36, pumps 42, reservoirs 40, laser power sources 32, coupling 28 and cables 34, 38 and tubing 44 are commercially available and form no part of this invention per se. The handle 24 and coupling 28 may be constructed of a rigid plastic such as a polycarbonate. The connecting tubing and fiber sheath may be constructed from extruded tubing made from a flexible plastic such as PVC. Other materials, such as plastics or composites, may be employed in various members. The materials employed must have sufficient mechanical strength to endure the forces involved in applying the laser surgical wand 100 to a beating human heart. In addition, materials must be appropriate to withstand the rigors of sterilization and meet all biocompatibility requirements.

In the embodiment of FIG. 1, the shaft 12 is made of a metallic material such as stainless steel. Additional embodiments of different construction will later be described.

As shown in FIG. 1, the shaft 12 maintains the axis A-A of fiber 20 at the guide tip 24 at an angle A to the axis B-B of the shaft 12 at the handle 18. In the embodiment of FIG. 1, this angle A is fixed. It will be appreciated other angles could be selected. In later embodiments, adjustability of the angle A is described.

The curvature of the shaft 12 at the distal end 24 of the laser surgical wand 10 is beneficial for assisting the physician in aligning the guide tip 24 in a perpendicular orientation to the myocardial tissue while maintaining a comfortable grip for the physician at the handle 18. A perpendicular alignment provides optimal coupling efficacy between the laser energy exiting the laser surgical wand 10 and the targeted cardiac tissue. The angle A can range from 0 to 135 degrees but is preferably between 20 and 90 degrees.

Referring to FIG. 3, the guide tip 24 is shown in longitudinal cross-section. The guide tip 24 is formed of plastic which is secured to the distal end 14 of the shaft 12. The guide tip 24 can be secured to the distal end 14 by any suitable means (e.g., threaded, adhered or other attachment means). The guide tip 24 has a centrally extending lumen 27 with a proximal end 27a in alignment with the annular passage 26 of the shaft 12. The stiffness of the fiber 20 maintains it alignment with the fiber axis A-A coaxial with the axis of the bore 27.

The optical fiber 20 extends through the lumen 27 with the discharge end 22 slightly spaced from a distal edge 50 of the guide tip 24. While the discharge end 22 could terminate at the distal edge 50, it is preferably spaced receded into the guide tip 24 by a spacing S of about 0.5 mm (and most preferably about 0.25 mm) from the distal edge 50.

It is desirable to have as close a spacing S of the discharge tip 22 to the distal edge 50 as possible to maximize laser energy penetration of myocardial tissue. The power density impinging on cardiac tissue decreases rapidly with increasing spacing S. However, a small spacing S (about 0.25 mm preferred) from the surface of the heart is desirable to prevent coagulation of biological products onto the face of the optical fiber. Build-up of tissue is undesirable because it can cause carbonization and spalling of the optical fiber face which reduces laser energy output from the optical fiber. If sufficient biological material is present in the vicinity of the optical fiber face, overheating and subsequent melting of the tip 24 can occur.

As shown in FIG. 3, the lumen 27 widens in a conical shape 29 to the distal edge 50. In a preferred embodiment, the widening starts a distance D of 1.0 mm proximal to the discharge tip 22 of the fiber 20 and widens at an angle of 45 degrees (measured as the angle of the conical surface 29 to the fiber axis A-A) to a maximum diameter at a lumen distal end 27b at the edge 50. At the proximal end 29a, the bore has a diameter of about 1.2 mm. At the distal end 27b, the bore 27 has a diameter of about 3.6. In a preferred embodiment, the fiber 20 may be either a 600 micron (1.0 mm) or 400 micron (0.72 mm) fiber.

The widening of the lumen 27 serves several purposes. Preferably, the laser energy source is a commercially available diode laser. Such laser energy sources have a high divergence angle for laser energy exiting the discharge tip 22 of the fiber 20. The widening of the distal end of the lumen 27 accommodates the discharge divergence of the laser energy. Further, the widening increases the surface area of the lumen 27 at the distal edge 50. This increases the area of the heart surface being washed by the fluid passing through the lumen 27.

At the distal edge 50 of the guide tip 24, the guide tip 24 does not present a flat surface opposing the heart tissue. Instead, the distal edge 50 is a radiused edge which presents a rounded ring opposing the heart surface. The edge 50 is radius at a radius of 0.75 mm over an arc of 90 degrees with an internal edge 50a beginning at the maximum diameter 27b of the lumen 27. The radiused or rounded edge 50 presents an atraumatic surface abutting the heart throughout the operating angle of the guide tip 24. The operating angle is the preferred angle of the axis A-A of the fiber 20 in the guide tip 24 to the surface of the heart. Preferably, this is within 45 degrees off perpendicular and, more preferably, within 30 degrees of perpendicular to ensure adequate coupling of the optics with the heart tissue. The outer surface 31 of the guide tip 24 is cylindrical and parallel to the fiber axis A-A. The rounded edge 50 blends into the cylindrical surface at 33 with a tangent of the edge 50 co-linear (in the same plane as axis A-A) with the cylindrical surface 31 so that no sharp edge is presented.

The guide tip 24 is circular in cross-section (taken perpendicular to the fiber axis A-A). The tip 24 has an outer cylindrical diameter of 5 mm and a cylindrical height of 6 mm. The discharge lumen 29 has a conical axis co-linear with the fiber axis A-A (which is collinear with the axis of light discharged from the fiber tip 22). The fluid flows from the guide tip in a direction parallel with axis A-A and flows radially outwardly in response to impinging upon the heart surface.

To further enhance the atraumatic nature of the guide tip 24, the tip 24 is formed of a soft material having a low coefficient of friction or lubricious-like nature against the heart tissue. Also, it is desirable that the material of the tip 24 be as transparent as possible to the therapeutic wavelength. For the preferred wavelengths described above, a preferred material is Deirin® acetal of DuPont Co., New Jersey (USA). While such material is generally transparent to the preferred laser energy wavelengths, the material may absorb some of the energy. Therefore, the fluid flowing through lumen 27 acts to cool the guide tip 24 as it flows through and around the tip 24.

In operation, the laser source 32 is adjusted to an appropriate power level, for example, from five to fifty watts. In addition, an appropriate flow rate for liquid cooling and flushing is set on infusion pump 42. An appropriate flow rate, for example, preferably is in the range of one to thirty milliliters per minute. The laser surgical wand 100 is then purged of air.

With the laser power source 32 and pump 42 activated, the surgeon applies the laser surgical wand 100 to epicardial tissue of the left or right atrium 102, 104 while tip 24 is in contact with the exterior surface of the heart 100 and held within the desired angle (preferably perpendicular or with 30 degrees of perpendicular) to the heart surface. The laser tip 22 is spaced from tissue by an unobstructed light pathway which is cleansed by the fluid from reservoir 40 (such fluid being non-absorbing or only minimally absorbing to the selected wavelength). With the present invention, the light impinging on the heart surface is a point which is then moved over the surface in a linear or curved path. Due to the unobstructed path, the light is a non-diffused or unmodified beam directed at the heart surface either perpendicularly of at an angle as described above.

The physician moves the probe 10 along the exterior surface of the heart in order to create lines of ablated (i.e., non-conducting) tissue by raising the temperature of the cardiac tissue to that required to achieve cellular death (typically 55° C.). For effective treatment of atrial fibrillation, the lines of ablated tissue must be transmural (i.e., cellular death extends the full thickness of the atrial tissue) and contiguous (no gaps of surviving tissue along the lines of cardiac ablation). The physician creates a pattern of lines which effectively divides the atria into electrical compartments. Commonly used patterns are called the MAZE pattern with its derivative patterns. If desired, the physician can easily re-trace the created pattern with additional application of energy. With the current invention, the physician can easier create complex, non-linear curved patterns or pathways around anatomical features (such as pulmonary veins).

Advantageously, the laser surgical wand 10 of the present invention utilizes laser energy that penetrates more deeply and is more highly focused than radio frequency energy. Laser energy is light that is converted into heat when absorbed by cardiac tissue. This allows the applied laser energy to first be scattered through the full thickness of the myocardium as light because of the optical properties of cardiac tissue and, secondarily, to be diffused as heat, because of the thermal properties of cardiac tissue. This allows for formation of lesions which have a smaller width than those created with more traditional radio frequency energy. Additionally, use of laser energy allows the creation of transmural lesions while there is full cardiac flow in the heart.

Radio frequency energy, on the other hand, relies on thermal diffusion to transmit energy from the epicardium to the endocardium. Because heat diffuses equally in all directions, radio frequency lesions are wider and its energy less focused than laser energy, especially in a unipolar mode. As a result, the cooling effect of the blood flow within the atria prevents subendocardial tissue from achieving the requisite temperature for cellar death. Therefore, to produce transmural lesions with radio frequency energy requires that cardiac flow be stopped by placing the patient on cardiac bypass. Otherwise, the surface of the heart must be heated to above a maximum (e.g., 75 degrees C.) to provide an adequate temperature gradient across the myocardium. However, at such temperatures, steam is created resulting in undesirable tissue damage and possible perforation. Any tissue removal in the thinned-walled atrium (about 2 mm thick in places) is undesirable.

Figure 4:
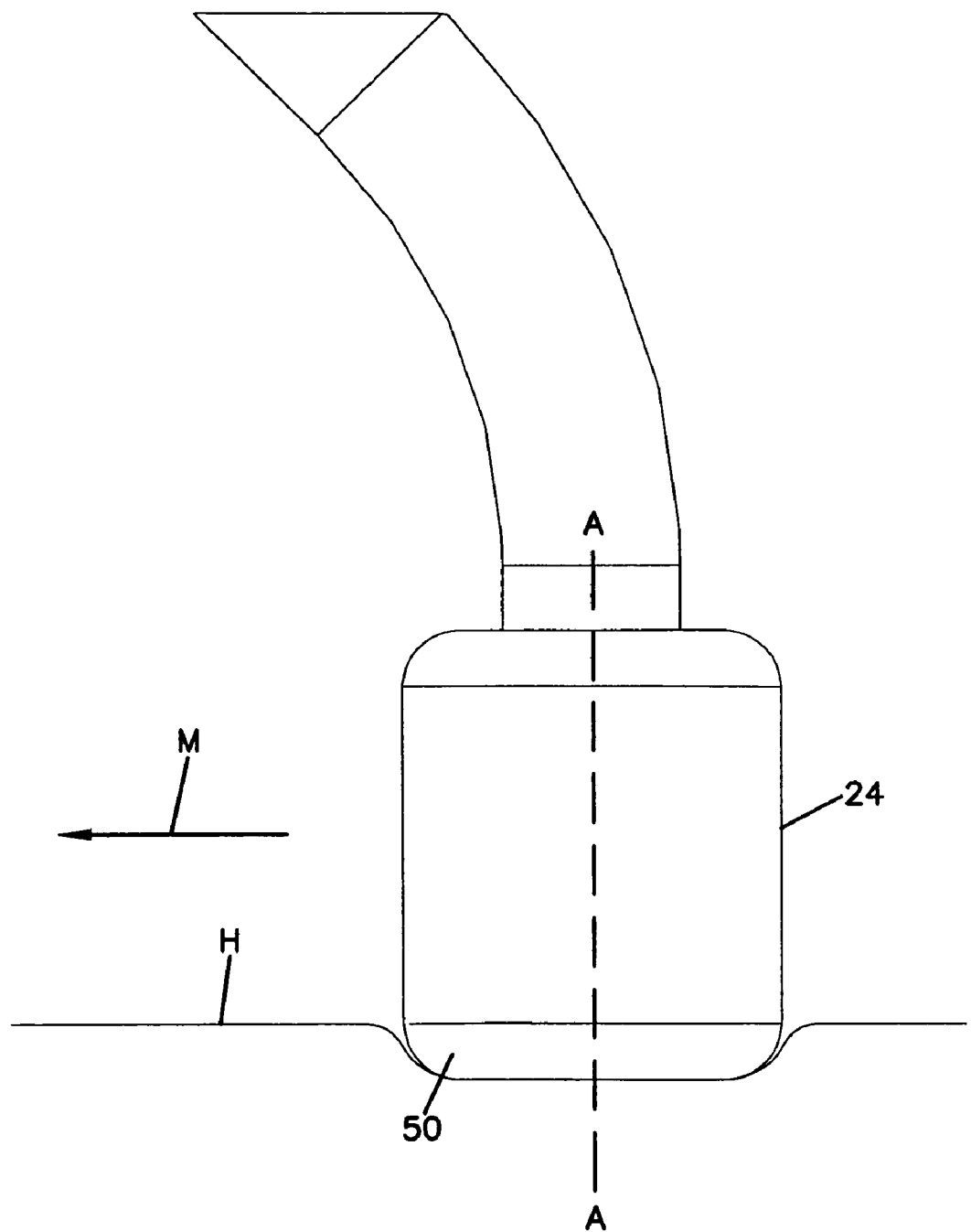
FIG. 4 is a longitudinal sectional view of the distal tip of the wand of FIG. 1 positioned against a tissue surface with an axis of a laser energy discharge substantially perpendicular to the tissue surface.
Figure 5:
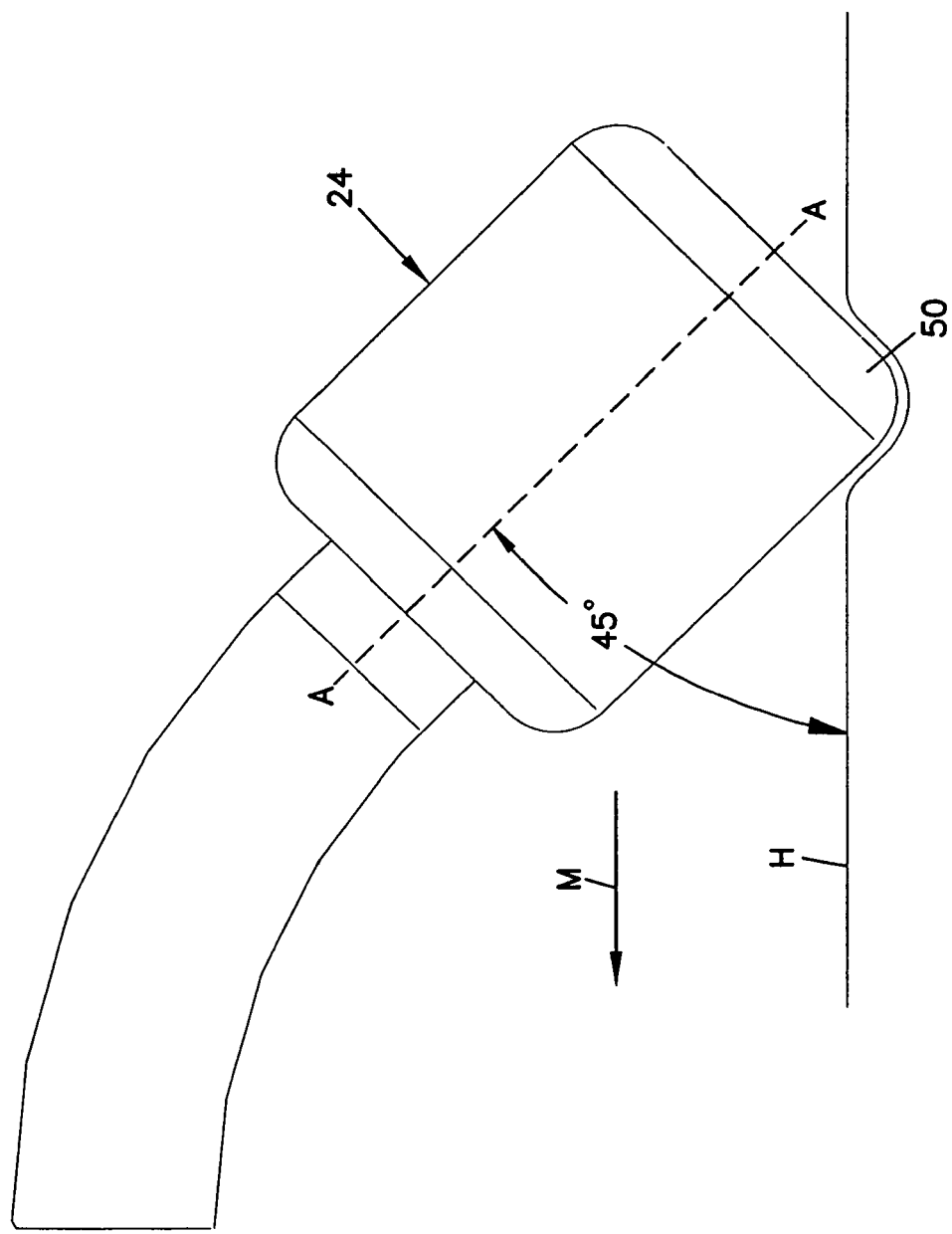
FIG. 5 is the view of FIG. 4 with the axis of the laser energy at an acute angle to the tissue surface.

The guide tip 24 permits the physician to slide the guide tip 24 over the heart surface in an atraumatic manner as the surgeon creates the ablation lines. FIGS. 4 and 5 illustrate the gliding movement. FIG. 4 shows the gliding motion (Arrow M) while the guide tip 24 is held in a most preferred perpendicular alignment to surface H the heart. FIG. 5 illustrates the gliding motion with the guide tip 24 at a less preferred but acceptable angle to the heart. In both, the rounded edge 50 opposes the heart surface to present a smooth atraumatic surface to the heart with no sharp edges opposing the heart. With an operating laser power of about 25 watts, the surgeon can create an ablation line by gliding the guide tip 24 over the heart surface at a rate of between about 1 to 5 cm of linear travel per minute.

Fluid flow through the lumen 27 cools the heart surface (to prevent carbonization) and cools the guide tip 24 while washing debris from a wide area around and below the fiber discharge end 22. Further, as the fluid flows between the guide tip 24 and the heart, the fluid acts as a lubricant further facilitating atraumatic gliding motion of the guide tip 24 over the heart surface.

Unlike laser treatment for ventricular ablation, the laser of the present invention is in continuous liner motion along the surface of the heart. The novel guide tip 24 permits atraumatic linear sliding motion not safely possible with prior art ventricular lasers which are adapted for anchoring in place at a specific location on the ventricular wall.

Optional Adjustable Tip

Referring to FIGS. 6-15, an additional modifications are is shown whereby component parts (e.g., the shaft 12) are constructed using malleable construction techniques, such as corrugations rather than a rigid tubular material. Alternatively, a highly elastic metal such as nitinol could be use. Nitinol is a well-known alloy of nickel and titanium which is malleable and highly elastic and can be formed with shape-memory properties. Malleability allows the shape of tip to be changed during a procedure. The ability to reconfigure tip allows surgeons to set the optimal geometric relationship between the laser surgical wand and the heart for applying laser energy. The maze procedure requires that linear lesions be placed on both the front and back side of the atria. When viewed physiologically, encirclement of the pulmonary veins on the backside of the heart is made easier if the shape is more acute than the shape required for lesions on the front side of the atria. By actively shaping the tip, procedure time is decreased and the likelihood of perforation is reduced making the procedure faster and safer for the patient.

In the embodiments of FIGS. 6-15, elements in common with the previous described embodiment are numbered identically throughout with the addition of subscripts to distinguish the embodiments.

Figure 6:
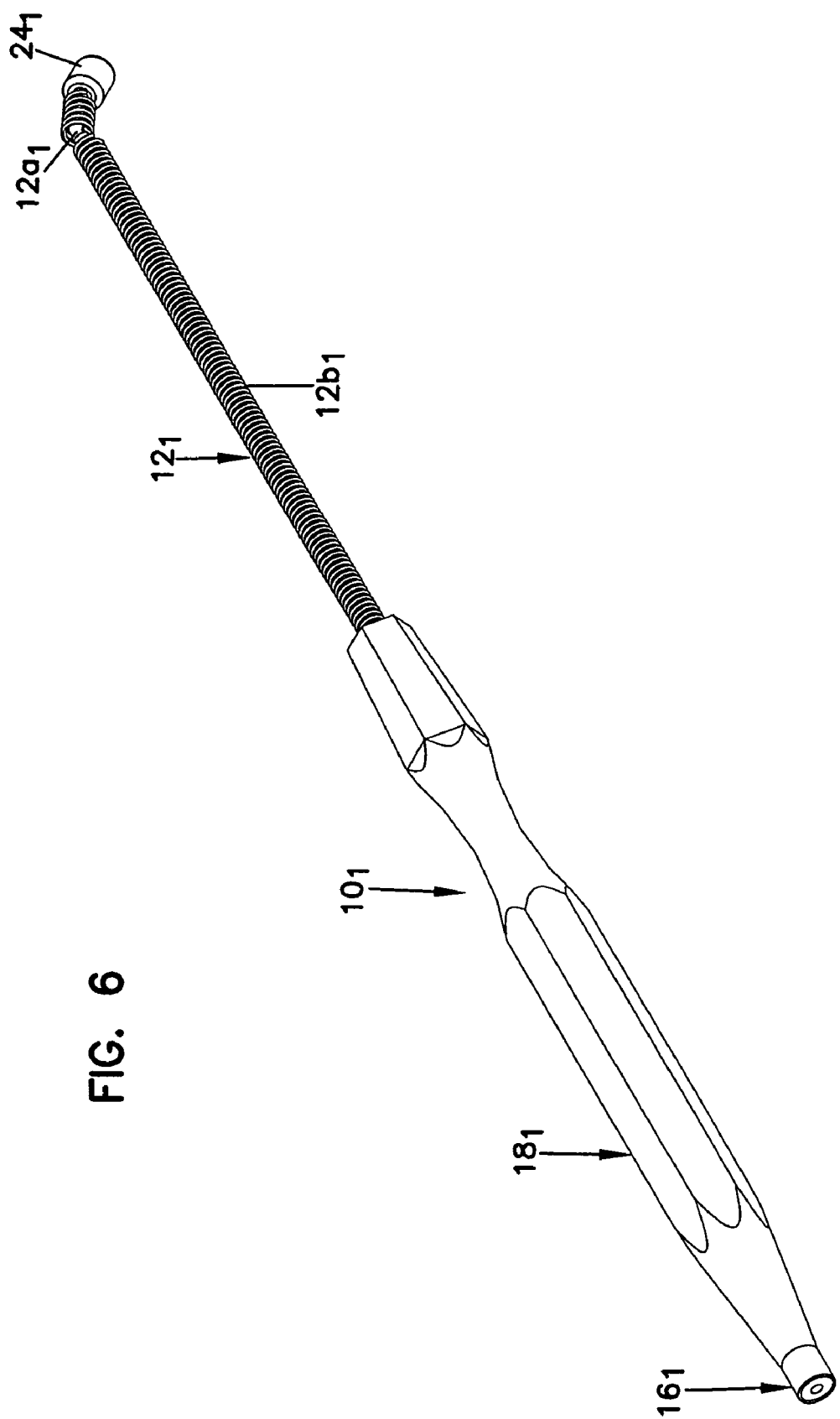
FIG. 6 is the view of FIG. 1 showing an alternative embodiment of the lesion formation tool to permit adjustability of an angle of a discharge guide tip.

In FIG. 6, the shaft $12_1$ from the handle $18_1$ to the guide tip $24_1$ is a composite including flexible tubing $12a_1$, which houses the lumen and optical fiber (not separately shown in FIG. 6). Tubing $12a_1$ may be plastic or metal (e.g., nitinol). A spring member $12b_1$ surrounds the flexible shaft component $12a_1$. The spring member $12b_1$ is formed of any suitable biocompatible material (such as nitinol or the like). The shaft $12_1$ can be bent and shaped at the desire of an operator to control the degree of bending and the relative angle between the guide tip $24_1$ and the shaft $12_1$ and to hold such shape after bending. The spring $12b_1$ prevents kinking of a metal tube $12a_1$ and maintains circularity of cross-section.

FIGS. 7 and 8 show an alternative embodiment where the shaft $12_2$ includes two components including a rigid outer sleeve $12a_2$ and a flexible, pre-formed inner tube $12b_2$, which contains the lumen $26_2$ housing the fiber (not separately shown). The inner sleeve $12b_2$ may be formed of pre-bent nitinol or plastic, which can be drawn into the outer shaft $12a_2$, which has a straight configuration. When the inner shaft $12b_2$ is moved relative to the rigid outer shaft $12a_2$, the inner shaft $12b_2$ returns, by the bias of its material, to the bent configuration shown in phantom lines in FIG. 7.

Figure 9:
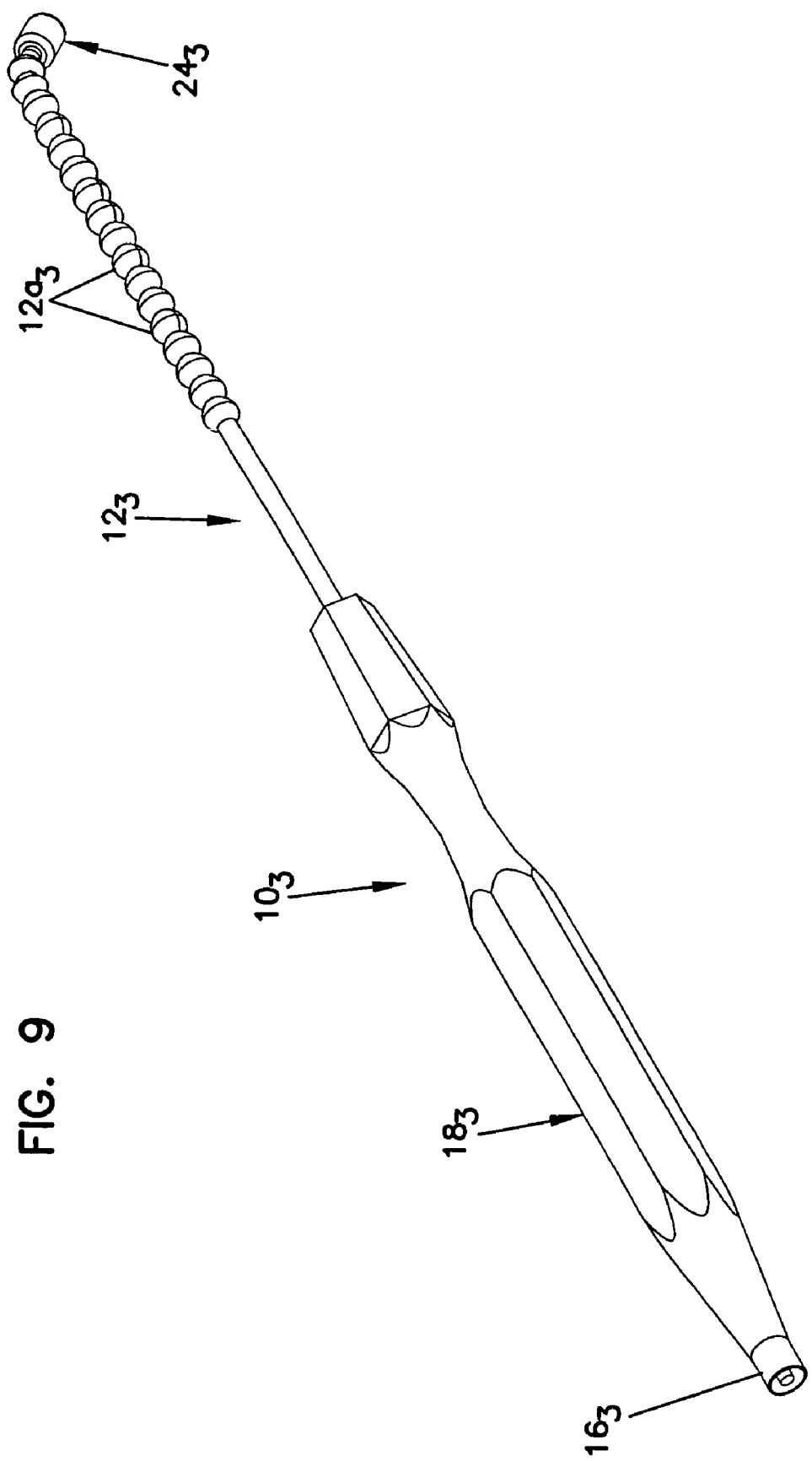
FIG. 9 is the view of FIG. 6 showing a still further alternative embodiment for adjustability.

In FIG. 9, the shaft $12_3$ includes a series of articulating bellows $12a_3$ which can be bent and manipulated by an operator to achieve a desired relative angle between the handle $18_3$ and guide tip $24_3$.

In FIGS. 10 and 11, the shaft includes two lumens $26_4$, $26a_4$ with a larger lumen $26_4$ housing the fiber (not shown) and a smaller lumen $26a_4$ containing a nitinol or other deformable rod or wire, which can be bent at the desire of an operator for a desired angle. This design permits compound curves in the shaft $12_4$.

Figure 13:
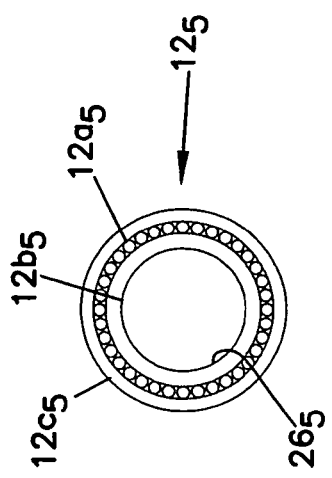
FIG. 13 is a view taken along line 13-13 of FIG. 12.
Figure 12:
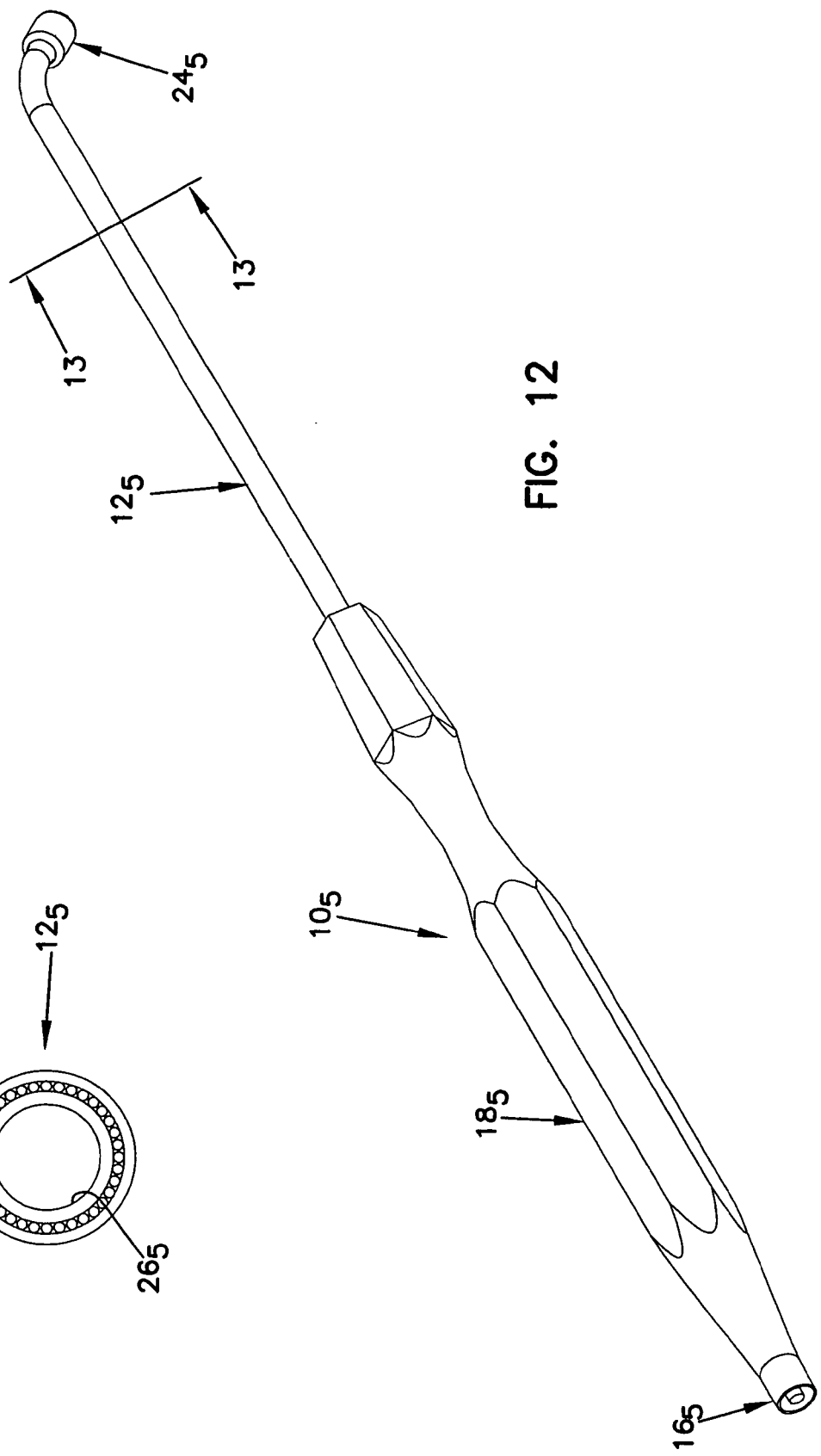
FIG. 12 is the view of FIG. 6 showing a still further embodiment of an adjustability feature.

FIGS. 12 and 13 show an embodiment where the shaft $12_5$ includes a wire braiding $12a_5$ sandwiched between inner sheath and outer plastic sheath $12b_5$, $12c_5$. The inner sheath $12b_5$ defines the lumen $26_5$, which contains the optical fiber (not shown). Both of the sheathings $12b_5$, $12c_5$ are flexible plastic construction. The operator can then bend the shaft $12_5$ with the braiding $12a_5$ maintaining the desired angle of curvature.

FIGS. 14 and 15 show an embodiment similar to that of FIGS. 10 and 11 except the second lumen $26a_6$ contains a pull wire $12a_6$ extending from a knob $18a_6$ to the guide tip $24_6$. Pulling on the wire $12a_6$ by turning the knob $18a_6$ bends the guide tip $24_6$ from a straight orientation (shown in phantom lines) to a curved orientation. This designs permits changing shape without re-positioning the location of the guide tip on the heart.

Imaging Capabilities

Figure 16:
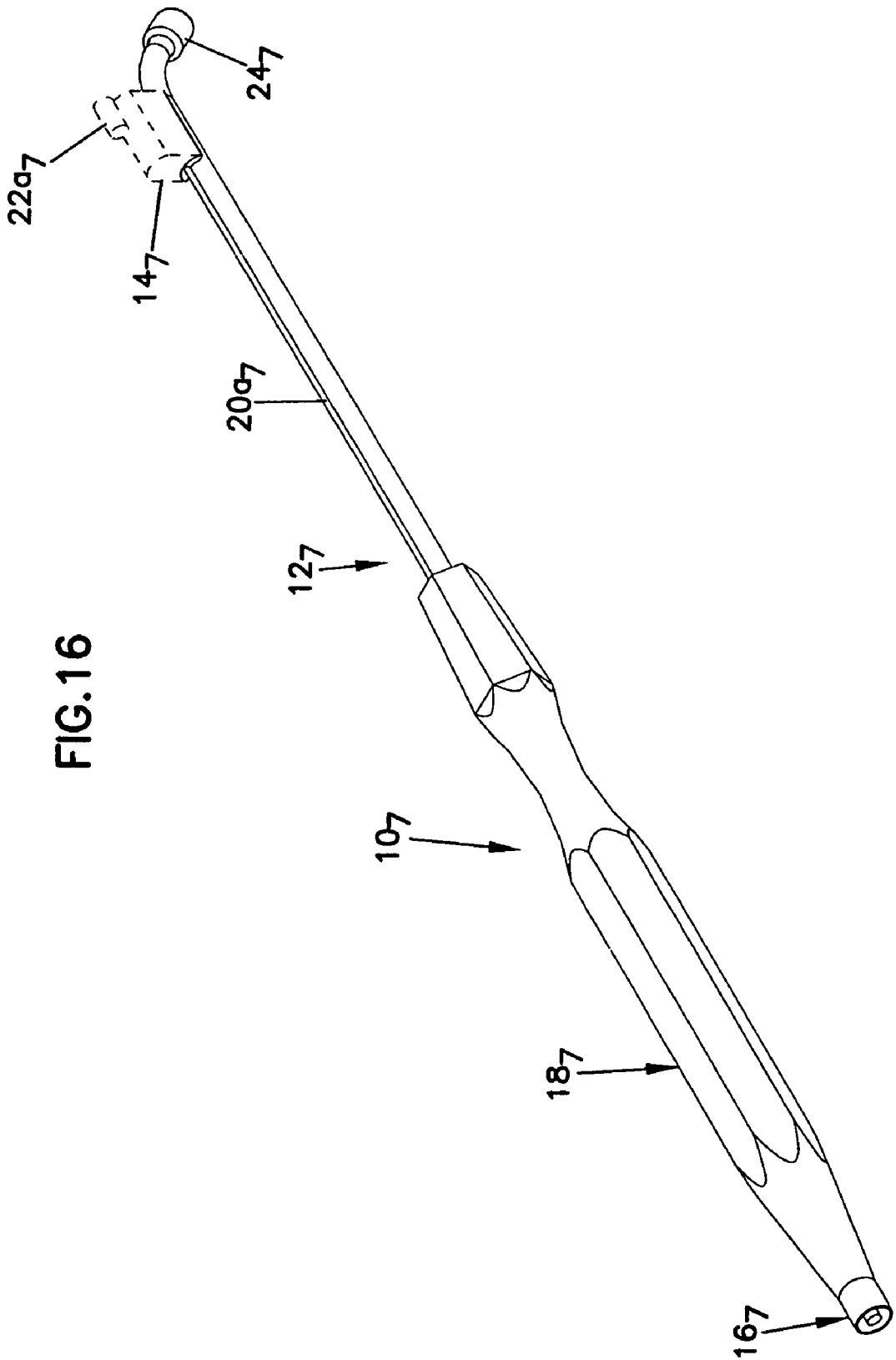
FIG. 16 is the view of FIG. 1 showing a visualization fiber near a distal end of a shaft.
Figure 17:
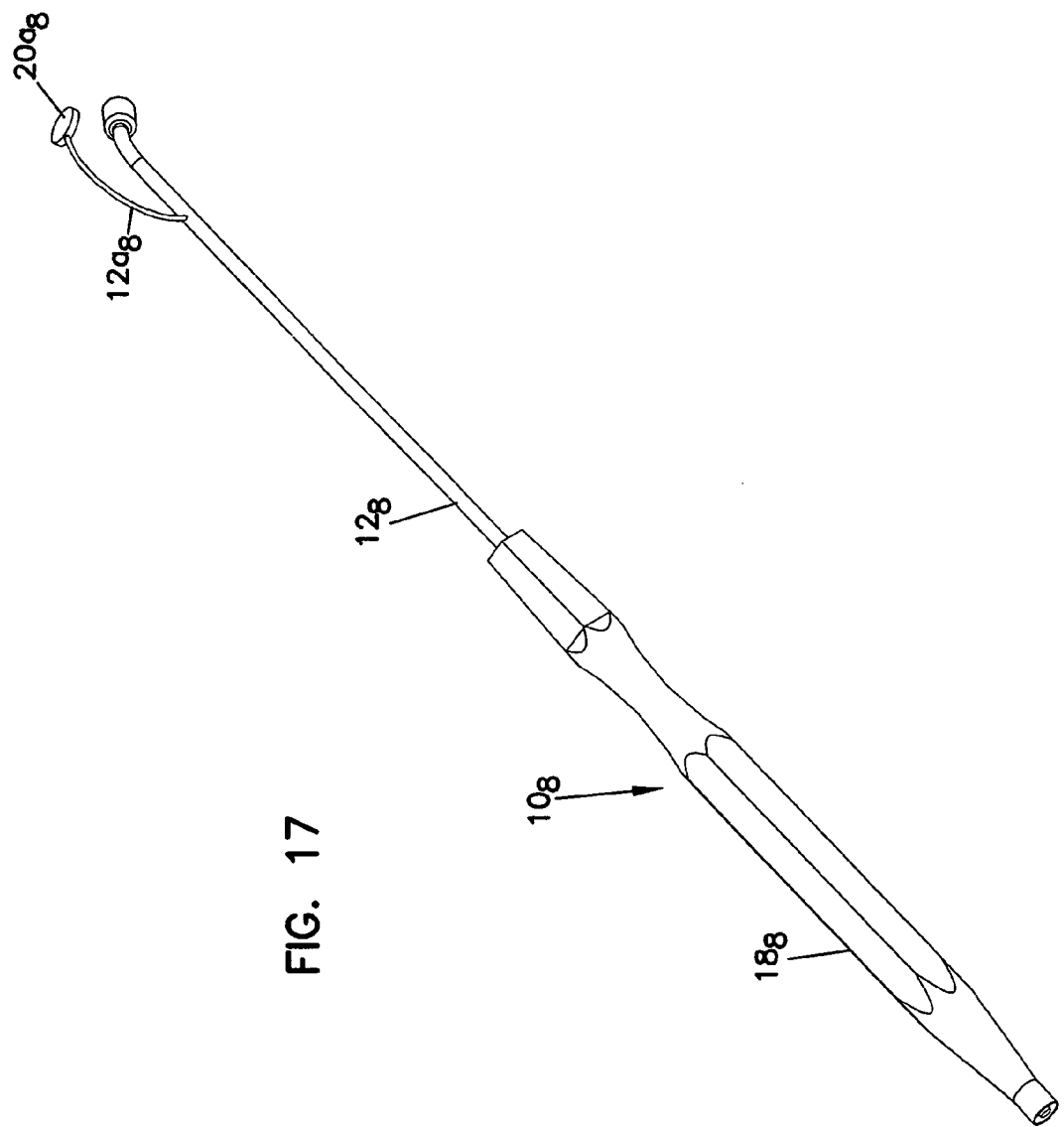
FIG. 17 is the view of FIG. 16 showing an alternative embodiment of a visualization fiber.

In addition to manipulating the angle of the guide tip 24, it may be desirable to clearly visualize the target area of tissue being ablated by the present invention. It has previously been described that a visually perceptible wavelength can be passed through the fiber 20 simultaneously with a therapeutic wavelength. However, the operator may not have adequate positioning relative to the guide tip 24 to fully view and inspect the ablation procedure. In such cases, it is desirable to add a second optical fiber to the laser wand to permit light to be passed back to the fiber to a camera or the like for permitting remote visualization. FIG. 16 illustrates such an option with FIG. 17 illustrating a modification for enhanced visualization. In the embodiments of FIGS. 16 and 17, elements in common with the previous described embodiment are numbered identically throughout with the addition of subscripts to distinguish the embodiments.

FIG. 16 shows an optical fiber $20_7$ carried on an external surface of the shaft $12_7$. A distal end $22a_7$ of the imaging optical fiber $20a_7$ is carried on the distal end of the shaft $12_7$ by an inflatable balloon $14_7$. Inflation of the balloon $14_7$ permits the operator to control the relative positioning of the imaging fiber tip $22a_7$ relative to the guide tip $24_7$ to enlarge the field of view as desired.

Figure 19:
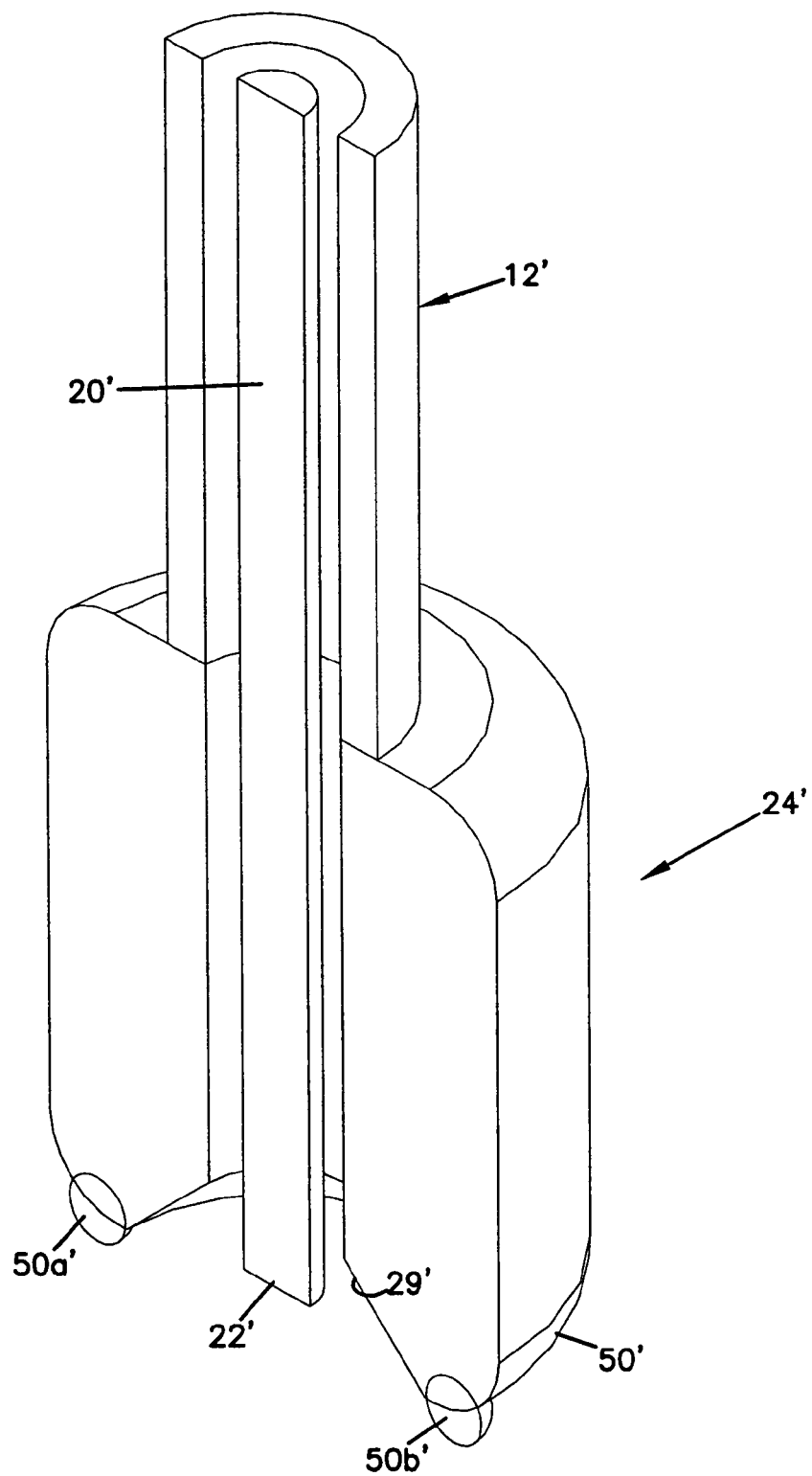
FIG. 19 a sectional view similar to that of FIG. 3 showing an alternative tip of the laser surgical wand of the present invention and illustrating optional sensing electrodes.
Figure 20:
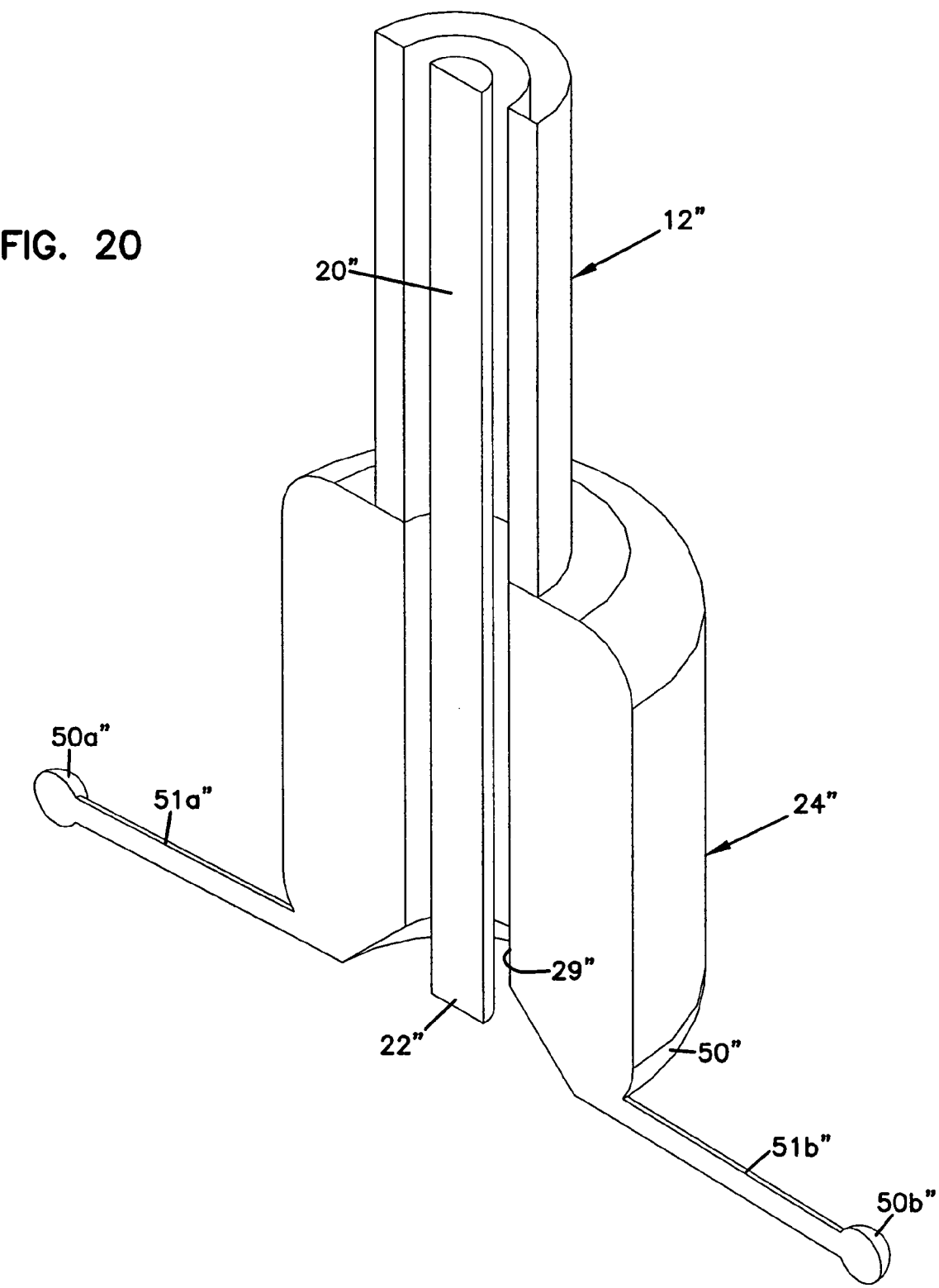
FIG. 20 is the view of FIG. 19 with a further embodiment illustrating optional electrodes on mechanical extensions.

In FIG. 17, a mirror $20a_8$ is carried on a malleable mounting post $12a_8$ at the distal end of the shaft $12_8$. The mounting post $12a_8$ can be pre-manipulated by an operator for targeting an area to be inspected through the mirror $20a_8$ or use the mirror to reflect light to the target area Optional Conductivity Testing As previously mentioned, it would be helpful if the surgeon could promptly discern whether a particular linear lesion is truly non-conducting at the time of the original procedure to permit correction at that time. This would enable prompt re-treatment if necessary. FIGS. 19 and 20 illustrate alternative embodiments of such an option. In FIGS. 19 and 20, elements in common with the structure of FIG. 3 are similar numbered with the addition of an apostrophe (in the case of FIG. 19) or double apostrophes (in the case of FIG. 20) to distinguish embodiments.

Unlike the previously described embodiments, a first electrode 50a' and a second electrode 50b' are preferably located on diametrically opposite sides of lumen 29' at the distal edge 50' to contact the heart surface for purposes that will be described. First electrode 50a' and second electrode 50b' are preferably separated by a distance on the order of several millimeters, preferably 3 to 6 mm. The distance selected is appropriate to ascertain that first electrode 50a' and second electrode 50b' can be readily applied to opposite sides of a linear lesion produced by the laser surgical wand. First electrode 50a' and second electrode 50b' are selected and adapted to sense an electrical potential in the local area of each.

Referring to FIG. 20, an alternative embodiment is shown including extension structures 51a", 51b" that are mechanically attached to the distal edge 50" of the guide tip 24". The extension structures 51a", 51b" support the electrodes 50a", 50b" at an increased distance from the guide tip 24". This arrangement provides greater spacing between the electrodes 50a", 50b" which permits more extensive testing for transmurality and electrical isolation of the lesion created by cardiac ablation.

With the embodiment of FIGS. 19 and 20, the surgeon performs the MAZE procedure as previously described without any use or activation of the electrodes 50a', 50b' or 50a", 50b".

Upon completion of the procedure, the surgeon retraces the created lines with laser surgical wand 10 so that first electrode 50a' or 50a" is on one side of the line and second electrode 50b' or 50b" is on the opposite side of the line. Electrical stimuli are then transmitted to the electrodes 50a', 50b' or 50a", 50b" from electrophysiology monitoring equipment 36 (FIG. 2) or similar instrumentation which are connected to the laser surgical wand using coupling 28. Electrical conductors (not shown) are formed into the shaft 12', 12" and electrically connect the coupling 28 to the electrodes 50a', 50b' or 50a", 50b".

The response of the cardiac tissue is observed. Tracing the created lines in this manner allows the surgeon to test to insure that two different electrical potentials exist on either side of the line. Differing electrical potentials indicate that a complete blockage of electrical energy transmission has been obtained. In the event different potentials are not indicated, the procedure of applying laser energy to the surface of the heart may be repeated as necessary until the desired effect of different potentials are obtained.

A major advantage of the current invention is the ability to create transmural lesions with full cardiac flow present, i.e. on a beating heart in an atraumatic manner without risk of perforation. With a beating heart, electrical isolation testing can optionally be done and, if gaps are found as evidence by lack of electrical isolation, these gaps can be repaired with additional application of laser energy. With radio frequency energy, the heart must be stopped which terminates all electrical activity. Thus, it is not possible to perform electrical isolation testing at the time of lesion creation. This essentially precludes repairing a failed line to obtain complete isolation unless the patient is placed on bypass a second time which is highly undesirable and unlikely. As a result, these patients remain in some degree of atrial fibrillation after surgery.

Another advantage of laser energy system and technique of the present invention is that it can be done concurrently with other beating heart procedures.

The present invention in other specific forms without departing from the spirit of any of the essential attributes thereof. Therefore, the illustrated embodiments should be considered, in all respects, as illustrative and not restrictive, reference being made to the appended claims rather than to the forgoing description to indicate the scope of the invention.

Optional Multiple Fibers

Figure 18:
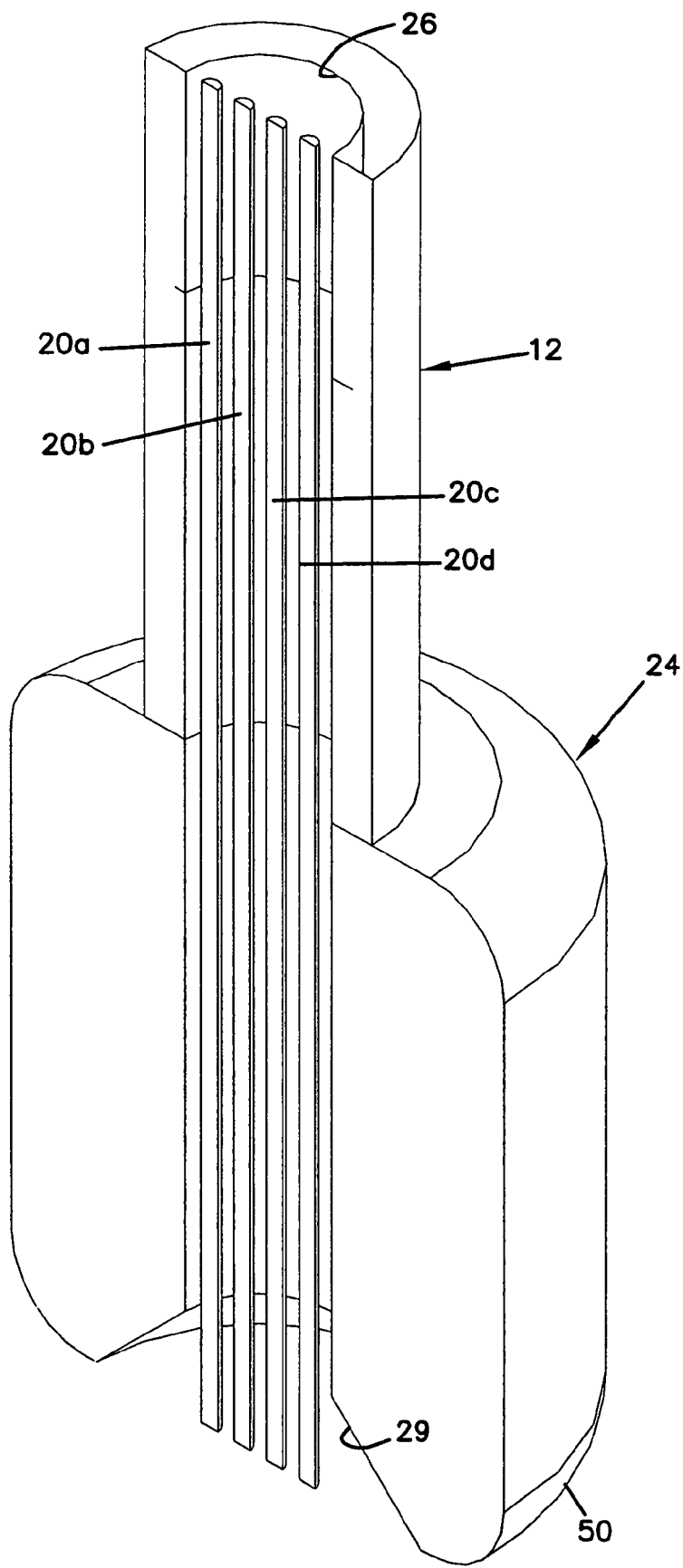
FIG. 18 is the view of FIG. 3 showing multiple fibers in an alternative embodiment of the invention.

Referring to FIG. 18, a modification replaces a single optical fiber 20 with a multiple of smaller fibers 20a, 20b, 20c, 20d. The fibers 20a-20d are placed collinear with the axis of the laser surgical wand. The use of multiple fibers 20a-20d focuses the laser energy which increases the probability of transmural lesions and also makes the lesion line thinner reducing the amount of cardiac tissue which is damaged. The use of multiple fibers 20a-20d is also more conducive to a laparoscopic design since smaller fibers are more flexible and can be bent in a tighter radius.

With any of the foregoing embodiments, access to the surface of the heart could be to either the endocardial or epicardial surface. Access could be either through a stemotomy or less invasive port access or other surgical access (e.g., open heart to access endocardial tissue) or could be catheter delivered. The procedure can be on a beating heart or on a heart with a patient supported on a by-pass machine.

In FIGS. 18-20, the collar 21 of FIG. 3 is not shown for ease of illustration only.

It has been shown how the objects of the invention have been achieved in a preferred embodiment. It is intended that such modifications and equivalents which will appear to one of ordinary skill in the art with the benefit of the teachings of the present invention shall be included within the scope of the claims.

What is claimed is:

1. A method for creating a lesion on a heart of a patient, said method comprising:
   a. accessing an atrial surface of the heart;
   b. positioning a lesion formation tool against said surface;
   c. forming a lesion with said tool by forming an elongated, narrow path of ablated tissue of the heart by moving said tool on said surface along said path and forming a lesion along said path wherein said lesion is formed by applying light energy to said heart to create said lesion;
   d. assessing a transmurality of said lesion by applying an electrical signal to said heart and assessing a conductivity of said signal across said lesion;
   wherein said assessing is performed by:
      placing at least two electrodes on the surface with a first electrode positioned on a first side of said lesion and with a second electrode placed on an opposite, second side of said lesion and
      moving the first and second electrodes by displacing the electrodes along a direction of the path while maintaining the first and second electrodes on the respective first and second sides; and
   wherein the applying of the electrical signal includes applying the signal to at least one of the first and second electrodes while moving the electrodes along the direction of the path.

2. A method according to claim 1 wherein said surface is an epicardial surface.

3. A method according to claim 1:
   wherein said surface is an endocardial surface.

4. A method according to claim 1 wherein said transmurality is assessed after formation of said lesion.

5. A method according to claim 1 wherein said transmurality is assessed during formation of said lesion.

6. A method according to claim 1 wherein said tool is manually moved along said path.

7. An apparatus for creating lesions on a patient's heart, said apparatus comprising:
   a. a lesion formation tool for creating a lesions on a heart surface, said tool including: an ablation element adapted for creating an elongated lesion on atrial tissue as the ablation element is moved along a desired lesion path, wherein said lesion formation tool includes a fiber optic waveguide for delivering coherent light at a preselected wavelength to said heart to create said lesion;
   b. electrodes adapted for connection to a source of an electrical signal to sense a transmurality of said lesion, said electrodes including at least first and second electrodes connected to the ablation element for movement therewith and positioned relative to the ablation element for the first electrode to be on a first side of the path and for the second electrode to be positioned on an opposite, second side of the path.

8. An apparatus according to claim 7 wherein said wavelength is selected from a range of about 470 nm to about 900 nm.

9. An apparatus according to claim 7 wherein said ablation element is disposed at a distal end of a manually movable handle.

* * * * *

UNITED STATES PATENT AND TRADEMARK OFFICE
CERTIFICATE OF CORRECTION

PATENT NO.        : 7,338,485 B2
APPLICATION NO.   : 11/066959
DATED             : March 4, 2008
INVENTOR(S)       : Brucker et al.

It is certified that error appears in the above-identified patent and that said Letters Patent is hereby corrected as shown below:

Col. 2, line 55: "sutara, at" should read --supra, at--

Col. 8, line 1: "a fill-thickness" should read --a full-thickness--

Col. 10, line 42: "is Deirin® acetal" should read --is Delrin® acetal--

Col. 15, lines 9-10: "a stemotomy or less" should read --a sternotomy or less--

Signed and Sealed this

Twenty-ninth Day of July, 2008

JON W. DUDAS
*Director of the United States Patent and Trademark Office*